US012306177B2

(12) United States Patent
Tang

(10) Patent No.: US 12,306,177 B2
(45) Date of Patent: May 20, 2025

(54) BLOOD BASED CONTROLS FOR COMPLEX PANEL

(71) Applicant: Becton, Dickinson and Company, Franklin Lakes, NJ (US)

(72) Inventor: Yuming Tang, San Jose, CA (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 386 days.

(21) Appl. No.: 17/240,122

(22) Filed: Apr. 26, 2021

(65) Prior Publication Data

US 2021/0356456 A1    Nov. 18, 2021

Related U.S. Application Data

(60) Provisional application No. 63/024,065, filed on May 13, 2020.

(51) Int. Cl.
  G01N 33/569    (2006.01)
  G01N 33/53     (2006.01)
  G01N 33/96     (2006.01)

(52) U.S. Cl.
  CPC ... *G01N 33/5306* (2013.01); *G01N 33/56966* (2013.01)

(58) Field of Classification Search
  None
  See application file for complete search history.

(56) References Cited

U.S. PATENT DOCUMENTS

| 5,641,637 A * | 6/1997 | Hudak | G01N 33/555 436/826 |
| 6,221,668 B1 * | 4/2001 | Ryan | G01N 33/96 436/63 |
| 2010/0105021 A1 | 4/2010 | May et al. | |
| 2013/0045529 A1 | 2/2013 | Goldberg et al. | |

(Continued)

FOREIGN PATENT DOCUMENTS

| EP | 0470810 A1 | 2/1992 |
| ES | 2464736 T3 | 6/2014 |
| WO | WO2019079851 A1 | 5/2019 |

OTHER PUBLICATIONS

Beckman Coulter (CYTO-TROL Control Cells Kit, 2018) (Year: 208).*

(Continued)

*Primary Examiner* — Ann Montgomery
*Assistant Examiner* — Chau N. B. Tran
(74) *Attorney, Agent, or Firm* — Darya C. Cheng; Bret E. Field; BOZICEVIC, FIELD & FRANCIS LLP

(57) ABSTRACT

Control compositions and methods of making the same are provided. Aspects of the control compositions include a first white blood cellular component including one or more positive control markers for white blood cells; a second cellular component including one or more positive control markers for hematopoietic stem/progenitor cells; and a third cellular component including one or more positive control markers for neoplastic cells, wherein the first white blood cellular component, the second cellular component, and third cellular component are fixed. Also provided are methods for using the control compositions as positive controls, e.g., in a flow cytometric assay, as well as kits for practicing the subject methods.

18 Claims, 10 Drawing Sheets

(56) References Cited

U.S. PATENT DOCUMENTS

2016/0123980 A1 5/2016 Evans et al.
2019/0298773 A1* 10/2019 Dimov ................. C12N 5/0638

OTHER PUBLICATIONS

Banko et al (Technologies for circulating tumor cell separation from whole blood, Journal of Hematology & Oncology 12:48 (2019)) (Year: 2019).*
Menon et al (Flow Cytometry Protocols for Surface and Intracellular Antigen Analyses of Neural Cell Types, J Vis Exp. 2014; (94): 52241.) (Year: 2014).*
Craig et al (Flow cytometric immunophenotyping for hematologic neoplasms, Blood (2008) 111 (8): 3941-3967.) (Year: 2008).*
BioLegend (Cell Markers, 2019). (Year: 2019).*
Maples (The use of Lyophilized Human Cells as Antigenic controls for Flow cytometry, 1993) (Year: 1993).*
Beckman Coulter (10C panels Clearllab Control Cells, 2019) (Year: 2019).*
Allard et al. (Tumor Cells Circulate in the Peripheral Blood of All Major Carcinomas but not in Healthy Subjects or Patients With Nonmalignant Diseases, Clinical Cancer Research vol. 10, 6897-6904,2004), (Year: 2004).*
Becton, Dickinson and Company, "BD OneFlow™ Solution on BD FACSCanto™ II and BD FACSLyric™ Flow Cytometers", www.bdbiosciences.com-eu, 8 pages, 2021.
Moloney, et al. "Efficiency and Health Economic Evaluations of BD OneFlow™ Flow Cytometry Reagents for Diagnosing Chronic Lymphoid Leukemia", Cytometry Part B (Clinical Cytometry) 96B:514-520 (2019).

* cited by examiner

BLOOD BASED CONTROLS FOR COMPLEX PANEL

CROSS-REFERENCE

Pursuant to 35 U.S.C. § 119 (e), this application claims priority to the filing date of U.S. Provisional Patent Application Ser. No. 63/024,065 filed May 13, 2020, the disclosure of which application is incorporated herein by reference in its entirety.

INTRODUCTION

Identifying specific cell populations is critical to research and diagnostic applications. Detecting cell markers, e.g., proteins expressed on the cell surface or in the cytoplasm, unique to a sub-population of cells is a common way to distinguish cell types in a heterogenous population of cells. Conventional cell identification assays include staining cells in a biological sample and detecting a marker or a combination of markers expressed by a population of cells to classify the cells as a specific cell type.

Immunophenotyping is a laboratory method that detects the presence or absence of markers for the purpose of identifying the presence and proportions of various cell populations of interest in a biological sample Immunophenotyping involves labeling cells with fluorophore-conjugated antibodies directed against specific cell markers and then flow cytometrically analyzing the marker expression profile of single cells to identify and quantify a given cell population. The analyzed cell populations may be separated into different groups based on their unique marker expression profile. Applications of immunophenotyping include detecting tumor markers to distinguish normal and cancerous cell populations Immunophenotyping can aid in the diagnosis, classification, treatment, and prognosis determination of several blood cancers such as, e.g., leukemias and lymphomas.

BD OneFlow™ (BD Biosciences, San Jose CA) is a commercially available flow cytometric immunophenotyping platform that facilitates the standardization of the characterization and diagnosis of various hematological malignancies. The platform offers antibody reagents provided in a dried, single-test tube format. The antibody reagents are designed as pre-configured, single-dose, ready-to-use 8-color reagents and may be stored at room temperature for an extended shelf life. The reagents are intended for flow cytometric immunophenotyping of normal and abnormal populations of white blood cells. The antibody reagents may be used for direct specimen staining without the need for antibody pipetting and are designed for use with a BD flow cytometer and software designated for in vitro diagnostic use. The BD OneFlow™ reagents are provided in the BD OneFlow™ Acute Leukemia Orientation Tube (ALOT), the BD OneFlow™ Lymphoid Screening Tube (LST), the BD OneFlow™ B-cell Chronic Lymphoproliferative Diseases Tube 1 (B-CLPD T1), the BD OneFlow™ Plasma Cell Screening Tube (PCST) tube, and the BD OneFlow™ Plasma Cell Dyscrasia (PCD) tube.

SUMMARY

Currently, there is no single process control which is positive for all OneFlow™ markers (e.g., all markers that may be detected by the reagents provided by each of the OneFlow™ kits) and compatible for use with OneFlow™ kits. The verification of the performance of OneFlow™ reagents and staining procedures must be conducted with a combination of multiple commercially available process controls that each individually lack all OneFlow™ markers or laboratory developed tests, which may limit operational efficiency and experimental accuracy. Many commercially available process controls are present in a liquid format, which may limit shelf life and stability.

Control compositions and methods of making the same are provided. Aspects of the control compositions include a first white blood cellular component including one or more positive control markers for white blood cells; a second cellular component including one or more positive control markers for hematopoietic stem/progenitor cells; and a third cellular component including one or more positive control markers for neoplastic cells, wherein the first white blood cellular component, the second cellular component, and third cellular component are fixed. Also provided are methods for using the control compositions as positive controls, e.g., in a flow cytometric assay, as well as kits for practicing the subject methods.

BRIEF DESCRIPTION OF THE DRAWINGS

The invention may be best understood from the following detailed description when read in conjunction with the accompanying drawings. Included in the drawings are the following figures.

DETAILED DESCRIPTION

Figure 1:
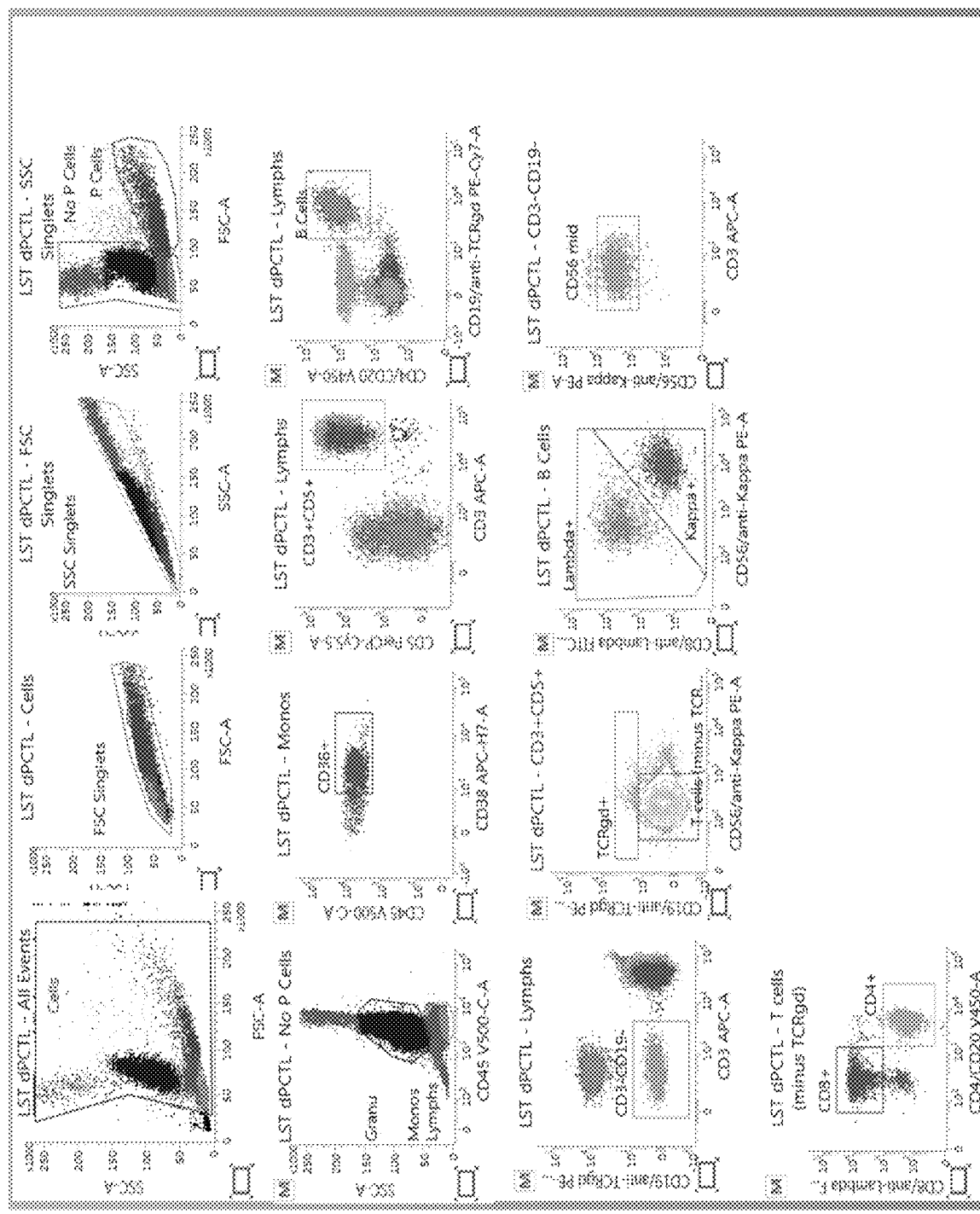
FIG. 1 provides results of a flow cytometric assay showing the detection of markers in a control composition labeled with BD OneFlow™ Lymphoid Screening Tube (LST) antibody reagents and gating of cell populations expressing the detected markers.

Control compositions and methods of making the same are provided. Aspects of the control compositions include a first white blood cellular component including one or more positive control markers for white blood cells; a second cellular component including one or more positive control markers for hematopoietic stem/progenitor cells; and a third cellular component including one or more positive control markers for neoplastic cells, wherein the first white blood cellular component, the second cellular component, and third cellular component are fixed. Also provided are methods for using the control compositions as positive controls, e.g., in a flow cytometric assay, as well as kits for practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing various aspects of the invention, the control compositions are described first in greater detail, followed by a review of embodiments of methods of using the control compositions in various applications, as well as a review of embodiments of kits that may include the control compositions.

Control Compositions

As summarized above, control compositions, e.g., flow cytometric control compositions, are provided. The control compositions may be used to validate the functionality or verify the performance of flow cytometer systems, methods, and reagents for use in flow cytometric assays. The control compositions of the invention may be positive control compositions. A positive control composition may be positive for (e.g., known to express) one or more markers of interest, e.g., cell surface markers or intracellular markers. A control composition of the present disclosure may be positive for all markers of interest, e.g., all markers that may be detected, in a flow cytometric assay, e.g., a flow cytometric diagnostic assay, and may be the only control composition required to serve as a positive control in a particular flow cytometric assay or a plurality of distinct flow cytometric assays. In certain embodiments, the control composition serves as a positive control in a flow cytometric immunophenotyping assay involving flow cytometrically analyzing a biological sample, e.g., a blood sample, from an individual to diagnose, classify, treat and/or determine prognosis of a blood cell cancer. In certain embodiments, the control composition may include all the markers that are used in flow cytometric immunophenotyping assays to distinguish between normal and neoplastic cells, e.g., normal and blood cancer cells, and classify various sub-populations of cells. In certain embodiments, the control composition may include more markers than all the markers needed in a given assay, e.g., immunophenotyping assay, to identify and characterize a particular population or populations of cells. In some embodiments, the control composition may include all the markers required in multiple distinct assays, where each individual assay is designed for analyzing one or more cell populations that are different from the cell populations analyzed by the other individual assays. In certain embodiments, the control composition may include more markers, e.g., 2 or more, 3 or more, 4 or more, 5 or more, 10 or more, etc., than all the markers needed in a given assay, e.g., immunophenotyping assay, to identify and characterize a particular population or populations of cells to aid in the diagnosis of a blood cancer or group of blood cancers. In some embodiments, the control composition may include all the markers required in multiple distinct assays, where each individual assay is designed for analyzing one or more cell populations characteristic of a particular blood cancer or group of blood cancers that are different from the cell populations analyzed by the other individual assays. In some cases, the control composition includes one or more cell types and all markers uniquely expressed by each of the cell types. In certain embodiments, the control composition may include more markers than all the markers needed in a given assay, e.g., immunophenotyping assay, to identify and characterize a disease or disorder, e.g., a blood cancer or group of blood cancers. In some embodiments, the control composition may include all the markers required in multiple distinct assays, where each individual assay is designed for identifying and characterizing a particular disease or disorder, e.g., a blood cancer or group of blood cancers, that is different from the disease or disorder, e.g., blood cancer or group of blood cancers, analyzed by the other individual assays.

In certain embodiments, the control composition comprises one or more positive control markers. As used herein, a "positive control marker" is a marker, e.g., protein, that is known to be present in the control composition, e.g., expressed by a cell in the control composition. Positive control markers of interest may include, e.g., markers that are the targets of binding members of a kit for use in a particular assay, e.g., a diagnostic assay. In some cases, a positive control marker includes a marker used to identify distinct cell populations in a cell lineage, to distinguish between cell types within a cell lineage, or to classify a cell population, e.g., a neoplastic cell population, in a sample. In some cases, the one or more positive control markers include cell surface markers. By cell surface marker is meant a marker, e.g., protein, expressed on the surface of a cell. The cell surface marker may be bound to or present within the cell membrane. In some embodiments, the cell surface marker includes a cell surface ligand, cell surface receptor, signaling molecule or components thereof. In some cases, the one or more positive control markers include intracellular markers. Intracellular markers are markers, e.g., proteins, that are present inside a cell, e.g., present in the cytoplasm. Intracellular markers may include, e.g., transcription factors, enzymes, cytoskeletal proteins, organelle proteins, etc.

The control composition may include, e.g., be positive for, any suitable number of positive control markers. In some cases, the control composition may include one or more markers selected from the group consisting of MPO (i.e., myeloperoxidase), CD79a (i.e., Immunoglobulin-associated alpha; IGA; B lymphocyte-specific MB1 protein; MB1; membrane-bound immunoglobulin IgM-Alpha), CD34 (i.e., hematopoietic progenitor cell antigen CD34), CD19 (i.e., B-lymphocyte antigen CD19), CD7 (i.e., Tp41), CD3 in its cytoplasmic form (cytoplasmic CD3; cyCD3) and cell surface form: (CD3) (i.e., T-cell antigen receptor complex; T3 complex), CD45 (i.e., Leukocyte-common antigen; LCA; T200 Glycoprotein; CD45R; homolog of LyS; B220; protein-tyrosine phosphatase receptor type C; PTPRC), CD20 (i.e., B-lymphocyte surface antigen B1; B1; Bp35; Leukocyte surface antigen Leu-16; membrane-spanning 4 domains subfamily A member 1), Lambda light chain (IGL; Igλ), Kappa light chain (IGK; Igκ), CD38 (i.e., ADP-Ribosyl Cyclase/Cyclic ADP-Ribose Hydrolase; ecto-nicotinamide adenine dinucleotide glycohydrolase), CD4 (i.e., T-cell antigen T4/Leu3), CD8 (i.e., p32; OKT8 T-cell antigen; T8 T-cell antigen), CD5 (i.e., T1; LEU1), TCRγδ, CD56 (i.e., cell adhesion molecule, neural 1; NCAM1; MSK39), CD23 (i.e., Fc fragment of IgE receptor II; FCER2; IgE-binding factor; IGEBF; C-Type Lectin Domain Family 4, member J; CLEC4J; receptor for Fc fragment of IgE, low affinity II; immunoglobulin E receptor, low affinity II), CD10 (i.e., membrane metalloendopeptidase; MME; common acute lymphocytic leukemia antigen; CALLA; Neprilysin; neutral endopeptidase; NEP; enkephalinase; atriopeptidase), CD79b (i.e., immunoglobulin-associated beta; IGB; immunoglobulin-associated B29 protein; B29), CD200 (i.e., OX2; membrane glycoprotein MRC OX2; MOX2), CD43 (i.e., sialophorin; SPN; leukosialin; LSN; leukocyte large sialoglycoprotein; CD43; GPL115), β2-Microglobulin (i.e., B2M), CD138 (i.e., syndecan1; SDC1; SYND1; Syndecan; SDC), CD28 (i.e., Tp44), CD27 (i.e., tumor necrosis factor receptor superfamily, member7; TNFRSF7; S152), CD117 (i.e., KIT protooncogene, receptor tyrosine kinase; KIT; v-kit Hardy-Zuckerman 4 feline sarcoma viral oncogene homolog; mast cell growth factor receptor; stem cell factor receptor; SCFR), CD81 (i.e., target of antiproliferative antibody 1; TAPA1), CD71 (i.e., transferrin receptor; TFRC; Transferrin Receptor 1; TFR1; TFR; TRFR), CD105 (i.e., endoglin; ENG), TdT (i.e., deoxynucleotidyltransferase, terminal; DNTT; terminal transferase; TDT). In some cases, the control composition includes a number of positive control markers ranging from 10% or more, 15% or more, 20% or more, 25% or more, 30% or more, 35% or more, 40% or more, 45% or more, 50% or more, 55% or more, 60% or more, or 65% or more positive control markers selected from the group consisting of MPO, CD79a, CD34, CD19, CD7, CD3 (cytoplasmic CD3 and cell surface CD3), CD45, CD20, Lambda light chain, Kappa light chain, CD38, CD4, CD8, CD5, TCRγδ, CD56, CD23, CD10, CD79b, CD200, CD43, β2-Microglobulin, CD138, CD28, CD27, CD117, CD81, CD71, CD105, TdT. In some cases, the control composition includes the positive control markers MPO, CD79a, CD34, CD19, CD7, CD3 (cytoplasmic CD3 and cell surface CD3), CD45, CD20, Lambda light chain, Kappa light chain, CD38, CD4, CD8, CD5, TCRγδ, CD56, CD23, CD10, CD79b, CD200, CD43, β2-Microglobulin, CD138, CD28, CD27, CD117, CD81, CD71, CD105, TdT. In some embodiments, the control composition includes all of the markers that are assayed for by all of the BD OneFlow line of products, including all 69 markers assayed for by the line of products available as of the filing date of this application (dbiosciences.com/eu/applications/clinical/blood-cell-disorders/oneflow-reagents/m/1641972/overview).

Aspects of the control composition include one or more cellular components. As used herein, a "cellular component" refers to, e.g., a cell, a population of cells, or a suspension of one or more cells or parts of a cell that are contained within the cell or produced by the cell. In some cases, the control composition includes a combination of different cellular components, e.g., distinct populations of cells. The control composition may have any suitable combination of cellular components to provide all the positive control markers of interest for an assay. Where the composition includes a combination of more than one cellular component, the number of different cellular components in the composition may vary, ranging in some instances from two to ten, such as two to five, e.g., two to three. In some cases, the control composition includes a first white blood cellular component including one or more positive control markers for white blood cells, a second cellular component including one or more positive control markers for hematopoietic stem/progenitor cells, and a third cellular component including one or more positive control markers for neoplastic cells, wherein the first white blood cellular component, the second cellular component, and third cellular component are fixed. The control composition may include any suitable amount of cells. In some cases, the control composition includes an amount of cells ranging from $1\times10^6$ to $3\times10^6$ cells, from $1.5\times10^6$ to $3\times10^6$ cells, from $2\times10^6$ to $3\times10^6$ cells, from $2.5\times10^6$ to $3\times10^6$ cells, from $2.6\times10^6$ to $3\times10^6$ cells, from $2.7\times10^6$ to $3\times10^6$ cells, or from $2.8\times10^6$ to $3\times10^6$ cells. The control composition may be a liquid or a dried composition.

The first white blood cellular component may include any suitable positive control markers for white blood cells, e.g., proteins expressed by white blood cells. A given marker is considered to be a suitable positive control marker for white blood cells if it is expressed by a white blood cell and may be used to identify a white blood cell from a heterogenous population of cells. In some cases, the positive control marker is expressed by a mature white blood cell or a differentiated white blood cell. In some cases, the first white blood cellular component includes one or more of the following positive control markers: MPO, CD79a, CD19, CD7, cytoplasmic CD3, cell surface CD3, CD20, Lambda light chain, Kappa light chain, CD4, CD8, CD5, TCRγδ, CD56, β2-Microglobulin. In some cases, the first white blood cellular component includes 5 or more, 10 or more, or 15 or more of the following positive control markers: MPO, CD79a, CD19, CD7, cytoplasmic CD3, cell surface CD3, CD20, Lambda light chain, Kappa light chain, CD4, CD8, CD5, TCRγδ, CD56, β2-Microglobulin.

The first white blood cellular component may include any suitable cell or part of a cell that provides the positive control markers for white blood cells. In some cases, the first white blood cellular component includes whole white blood cells. As used herein, a "white blood cell" or "leukocyte" refers to a cell that plays a role in the body's host immune defense system. White blood cells may include, but are not limited to, monocytes, macrophages, dendritic cells, mast cells, natural killer cells, granulocytes (basophils, eosinophils, neutrophils), and lymphocytes (B, and T lymphocytes), The first white blood cellular component may be prepared according to any suitable method known in the art, as described below. In some cases, the first white blood cellular component includes whole white blood cells and is substantially free of whole red blood cells. In some cases, the first white blood cellular component includes an amount of purified or enriched whole white blood cells. In some cases, the first white blood cellular component is prepared from whole blood contacted with a lysing agent for lysing red blood cells. In some cases, the first white blood cellular component prepared with lysing reagent includes remnants or portions of lysed red blood cells including, e.g., cell membranes and cytoplasmic contents of lysed red blood cells. In some cases, the first white blood cellular component prepared with lysing reagent includes an amount of lysing agent, e.g., lysing agent that has not been removed after red blood cell lysis or excess lysing agent remaining after a wash step. The first white blood cellular component may include any suitable number of cells. In some cases, the first white blood cellular component includes an amount of cells that ranges from 80% to 95%, from 85% to 95%, or from 90% to 95% of total cells of the control composition. In some cases, the first white blood cellular component comprises an amount of cells ranging from $2\times10^6$ to $2.5\times10^6$ cells, from $2\times10^6$ to $3\times10^6$ cells, from $2.2\times10^6$ to $3\times10^6$ cells, from $2.3\times10^6$ to $3\times10^6$ cells, from $2.4\times10^6$ to $3\times10^6$ cells, or from $2.5\times10^6$ to $3\times10^6$ cells.

The second cellular component may include any suitable positive control markers for hematopoietic stem/progenitor cells, e.g., proteins expressed by hematopoietic stem/progenitor cells. In some cases, the second cellular component includes the following positive control markers: CD34, CD117, CD105, CD71, TdT. In some cases, the second cellular component includes 2 or more, 3 or more, 4 or more, or 5 or more of the following positive control markers: CD34, CD117, CD105, CD71, TdT.

The second cellular component can include any suitable cell or part of a cell that provides the positive control markers for hematopoietic stem/progenitor cells. In some cases, the second cellular component includes hematopoietic stem/progenitor cells. As used herein, the term "hematopoietic stem cell (HSC)" refers to a cell with multi-lineage hematopoietic differentiation potential and sustained self-renewal activity. "Self-renewal" refers to the ability of a cell to divide and generate at least one daughter cell with the identical (e.g., self-renewing) characteristics of the parent cell. The second daughter cell may commit to a particular differentiation pathway. For example, a self-renewing hematopoietic stem cell divides and forms one daughter stem cell and another daughter cell committed to differentiation in the myeloid or lymphoid pathway. A committed progenitor cell has typically lost the self-renewal capacity, and upon cell division produces two daughter cells that display a more differentiated (i.e., restricted) phenotype. Hematopoietic stem cells have the ability to regenerate long term multi-lineage hematopoiesis (e.g., "long-term engraftment") in individuals receiving a bone marrow or cord blood transplant. The hematopoietic stem cells used in control composition according to embodiments of the invention may be derived from any one or more of the following sources: fetal tissues, cord blood, bone marrow, peripheral blood, mobilized peripheral blood, a stem cell line, or may be derived ex vivo from other cells, such as embryonic stem cells, induced pluripotent stem cells (iPS cells) or adult pluripotent cells. The cells from the above listed sources may be expanded ex vivo using any method acceptable to those skilled in the art prior to use. In some cases, the hematopoietic stem cells may be isolated from any of the above-listed sources (e.g., bone marrow) and cultured in vitro. If the cells used are derived from an immortalized stem cell line, further advantages may be realized in the ease of obtaining and preparation of cells in adequate quantities. As used herein, the term "hematopoietic progenitor cells" encompasses pluripotent cells capable of differentiating into several cell types of the hematopoietic system, including, but not limited to, granulocytes, monocytes, erythrocytes, megakaryocytes, B-cells and T-cells.

Hematopoietic progenitor cells are committed to the hematopoietic cell lineage and generally do not self-renew. The term "hematopoietic progenitor cells" encompasses short term hematopoietic stem cells (ST-HSCs), multi-potent progenitor cells (MPPs), common myeloid progenitor cells (CMPs), granulocyte-monocyte progenitor cells (GMPs), and megakaryocyte-erythrocyte progenitor cells (MEPs). The term "hematopoietic progenitor cells" does not encompass hematopoietic stem cells capable of self-renewal (herein referred to as "hematopoietic stem cells"). The presence of hematopoietic progenitor cells can be determined functionally as colony forming unit cells (CFU-Cs) in complete methylcellulose assays, or phenotypically through the detection of cell surface markers using assays known to those of skill in the art.

The hematopoietic stem/progenitor cells may be isolated from any suitable source. In some embodiments, the hematopoietic stem/progenitor cells of the control composition are derived from bone marrow. In some embodiments, the hematopoietic stem/progenitor cells of the control composition are derived from umbilical cord blood and/or placental cord blood (e.g., from a single human and collected at birth of said human, or from a pool of two or more different humans at birth). In other embodiments, the isolated hematopoietic stem/progenitor cells are derived from peripheral blood (e.g., mobilized peripheral blood stem cells). In some embodiments, the isolated hematopoietic stem/progenitor cells are derived from a single human, while in other embodiments, the isolated HSPC are derived from two or more humans (where the two or more humans can be, but are not limited to, humans of the same race or humans of the same ethnicity). Suitable HSPCs include, e.g., normal human primary bone marrow CD34+ cells (ATCC® PCS-800-012™), human CD34+ progenitor cells from cord blood of a single donor (PromoCell® C-12921).

The second cellular component may include any suitable number of cells. In some cases, the second cellular component includes an amount of cells that ranges from 1% to 10%, from 3% to 10%, or from 5% to 10% of total cells of the control composition. In some cases, the second cellular component includes an amount of cells ranging from $0.1\times10^6$ to $0.2\times10^6$ cells, from $0.1\times10^6$ to $0.3\times10^6$ cells, $0.1\times10^6$ to $0.5\times10^6$ cells, or from $0.1\times10^6$ to $1\times10^6$ cells.

The third cellular component may include any suitable positive control markers for neoplastic cells, e.g., proteins expressed by neoplastic cells. In some cases, the third cellular component includes the following positive control markers: CD38, CD23, CD10, CD79b, CD200, CD43, CD56, CD45, CD28, CD27, CD81, CD138. In some cases, the third cellular component includes 5 or more, 10 or more, or 15 or more of the following positive control markers: CD38, CD23, CD10, CD79b, CD200, CD43, CD56, CD45, CD28, CD27, CD81, CD138.

The third cellular component can include any suitable cell or part of a cell that expresses the positive control markers for neoplastic cells. In some cases, the third cellular component includes neoplastic cells. The third cellular component may be prepared from any suitable source of neoplastic cells such as, e.g., a neoplastic cell line.

As used herein, "neoplastic cells" refer to cells which exhibit relatively autonomous growth, so that they exhibit an aberrant growth phenotype characterized by a significant loss of control of cell proliferation. Neoplastic cells can include cells which may be actively replicating or in a temporary non-replicative resting state (G 1 or G 0); similarly, neoplastic cells may include cells which have a well-differentiated phenotype, a poorly-differentiated phenotype, or a mixture of both type of cells. Thus, not all neoplastic cells are necessarily replicating cells at a given timepoint. Neoplastic cells may encompass aberrant immature and mature cells of a particular cell lineage. Neoplastic cells may encompass such cells in benign neoplasms and cells in malignant neoplasms. Malignant neoplastic cells are frequently referred to as cancer, typically termed carcinoma if originating from cells of endodermal or ectodermal histological origin, or sarcoma if originating from cell types derived from mesoderm.

In some cases, the neoplastic cells include hematologic cancer cells or blood cancer cells. The terms "hematologic cancer" or "blood cancer" refers to cancers of cells derived from the blood. In certain embodiments, the blood cancer cells include abnormal white blood cells such as, e.g., lymphoma cells, leukemia cells, or multiple myeloma cells. In some cases, the neoplastic cells include neoplastic mature lymphocyte populations of B, T, and NK cell lineages obtained from peripheral blood, bone marrow, and lymph node tissue. In certain embodiments, the neoplastic cells include neoplastic immature populations of hematopoietic stem/progenitor cells (lymphoid and non-lymphoid lineage) obtained from bone marrow and peripheral blood. In certain embodiments, the control composition includes neoplastic cells obtained from a cancer cell line, where the cancer is selected from the group consisting of acute lymphoblastic leukemia; non-lymphoid acute leukemia; B, T and myeloid acute leukemias (e.g., BCP-ALL, T-ALL); B-cell chronic lymphoproliferative diseases (e.g., chronic lymphocytic leukemia (CLL)); a plasma cell disorder (e.g., multiple myeloma); undifferentiated leukemia (AUL), and mixed phenotype acute leukemia (MPAL). In certain embodiments, the control composition includes neoplastic cells obtained from a cancer cell line, where the cancer is selected from the group consisting of multiple myeloma, acute lymphocytic leukemia, myeloid leukemia including acute myeloid leukemia and chronic myelogenous leukemia, chronic lymphocytic leukemia, small lymphocytic lymphoma, non-Hodgkin's lymphoma, Hodgkin's lymphoma, mantle cell lymphoma, follicular lymphoma, Waldenstrom's macroglobulinemia, B-cell lymphoma and diffuse large B-cell lymphoma, precursor B-lymphoblastic leukemia/lymphoma, B-cell chronic lymphocytic leukemia/small lymphocytic lymphoma, B-cell prolymphocytic leukemia, lymphoplasmacytic lymphoma, splenic marginal zone B-cell lymphoma (with or without villous lymphocytes), hairy cell leukemia, plasma cell myeloma/plasmacytoma, extranodal marginal zone B-cell lymphoma of the MALT type, nodal marginal zone B-cell lymphoma (with or without monocytoid B cells), Burkitt's lymphoma; precursor T-lymphoblastic lymphoma/leukemia, T-cell prolymphocytic leukemia, T-cell granular lymphocytic leukemia, aggressive NK cell leukemia, adult T-cell lymphoma/leukemia (HTLV 1-positive), nasal-type extranodal NK/T-cell lymphoma, enteropathy-type T-cell lymphoma, hepatosplenic .gamma.-.delta. T-cell lymphoma, subcutaneous panniculitis-like T-cell lymphoma, mycosis fungoides/Sezary syndrome, anaplastic large cell lymphoma (T/null cell, primary cutaneous type), anaplastic large cell lymphoma (T-/null-cell, primary systemic type), peripheral T-cell lymphoma not otherwise characterized, angioimmunoblastic T-cell lymphoma, polycythemia vera (PV), myelodysplastic syndrome (MDS), indolent Non-Hodgkin's Lymphoma (iNHL) and aggressive Non-Hodgkin's Lymphoma (aNHL).

The third cellular component may include any suitable number of cells. In some cases, the third cellular component includes an amount of cells that ranges from 1% to 10%, from 3% to 10%, or from 5% to 10% of total cells of the control composition. In some cases, the third cellular component includes an amount of cells ranging from $0.1 \times 10^6$ to $0.2 \times 10^6$ cells, from $0.1 \times 10^6$ to $0.3 \times 10^6$ cells, $0.1 \times 10^6$ to $0.5 \times 10^6$ cells, or from $0.1 \times 10^6$ to $1 \times 10^6$ cells. Suitable neoplastic cells can include, e.g., myeloma cells from one or more of the following cell lines and their respective commercial sources: U266 (ATCC® TIB-196™), OPM-2 (DSMZ, Cat no: ACC50), RPMI-8226 (ATCC® CCL-155™), MM1S (ATCC® CRL-2974™). Suitable neoplastic cells can include, e.g., lymphoma cells from one or more of the following cell lines and their respective commercial sources: DB (ATCC® CRL-2289™), HT (ATCC® CRL-2260™), BC-3 (ATCC® CRL-2277™), CA46 (ATCC® CRL-1648™), Raji (ATCC® CCL-86™), Daudi (ATCC® CCL-213™), GA-10-Clone-4 (ATCC® CRL-2393™), HH (ATCC® CRL-2105™), H9 (ATCC® HTB-176™). Suitable neoplastic cells can include, e.g., leukemia cells from one or more of the following cells lines and their respective commercial sources: KASUMI-1 (ATCC® CRL-2724™); HL-60 (ATCC® CCL-240™); THP-1 (ATCC® TIB-202™); K-562 (ATCC® CCL-243™); RS4; 11 (ATCC® CRL-1873™); MOLT-4 (ATCC® CRL-1582™); CCRF-CEM (ATCC® CCL-119™).

In certain embodiments, the control composition is a dried composition. A dried control composition may be a composition that includes a low amount of solvent. For example, a dried control composition may include a low amount of a liquid, such as water. In some cases, a dried control composition includes substantially no solvent. For instance, dried control compositions may include substantially no liquid, such as water. In certain embodiments, a dried control composition includes 25 wt % or less solvent, such as 20 wt % or less, or 15 wt % or less, or 10 wt % or less, or 5 wt % or less, or 3 wt % or less, or 1 wt % or less, or 0.5 wt % or less solvent. In some cases, a dried control composition is not a fluid. In some cases, a dried control composition is substantially a solid. For example, a dried control composition may have a high viscosity, such as a viscosity of 10,000 cP or more, or 25,000 cP or more, or 50,000 cP or more, or 75,000 cP or more, or 100,000 cP or more, or 150,000 cP or more, or 200,000 cP or more, or 250,000 cP or more at standard conditions. In some embodiments, the control composition may be present in an amount ranging from 0.1 mg to 1000 mg, such as from 0.1 mg to 900 mg, such as from 0.1 mg to 800 mg, such as from 0.1 mg to 700 mg, such as from 0.1 mg to 600 mg, such as from 0.1 mg to 500 mg, such as from 0.1 mg to 400 mg, or 0.1 mg to 300 mg, or 0.1 mg to 200 mg, or 0.1 mg to 100 mg, 0.1 mg to 90 mg, or 0.1 mg to 80 mg, or 0.1 mg to 70 mg, or 0.1 mg to 60 mg, or 0.1 mg to 50 mg, or 0.1 mg to 40 mg, or 0.1 mg to 30 mg, or 0.1 mg to 25 mg, or 0.1 mg to 20 mg, or 0.1 mg to 15 mg, or 0.1 mg to 10 mg, or 0.1 mg to 5 mg, or 0.1 mg to 1 mg, or 0.1 mg to 0.5 mg. In some embodiments, the control composition may be present in an amount ranging from 0.1 g to 10 g, or 0.1 g to 5 g, or 0.1 g to 1 g, or 0.1 g to 0.5 g.

In some instances, the control compositions are lyophilized compositions. In certain cases, a lyophilized control composition is a composition where water has been removed from the composition by sublimation, where the water in the composition undergoes a phase transition from a solid to a gas. For example, a lyophilized composition may be a composition where water has been removed from the composition by freezing the composition (e.g., freezing water in the composition) and then reducing the pressure surrounding the composition such that the water in the composition undergoes sublimation. In certain instances, a lyophilized control composition includes water in a low amount, such as 25% or less, or 20% or less, or 15% or less, or 10% or less, or 9% or less, or 8% or less, or 7% or less, or 6% or less, or 5% or less, or 4% or less, or 3% or less, or 2% or less, or 1% or less, or 0.5% or less, or 0.25% or less, or 0.1% or less water as measured by Karl Fischer (KF) titration. In some cases, a lyophilized composition has 3% or less water as measured by Karl Fischer titration. In some cases, a lyophilized composition has 1% or less water as measured by Karl Fischer titration. In some cases, a lyophilized composition has 0.5% or less water as measured by Karl Fischer titration. Lyophilized compositions may include additives and/or excipients, such as a stabilizer. In some cases, the lyophilized composition includes a stabilizer, such as a sugar or a polyalcohol. Sugars and polyalcohols suitable for use in lyophilized compositions include sugars that are compatible with the other reagents, buffers, and sample components being used. Examples of suitable sugars include, but are not limited to, sucrose, maltose, trehalose, 2-hydroxypropyl-beta-cyclodextrin (β-HPCD), lactose, glucose, fructose, galactose, glucosamine, and the like, and combinations thereof. In certain instances, the sugar is a disaccharide. For example, the disaccharide may be sucrose. Examples of suitable polyalcohols include, but are not limited to, mannitol, glycerol, erythritol, threitol, xylitol, sorbitol, and the like, and combinations thereof.

In certain embodiments, the control composition is a liquid composition. The liquid composition may include any suitable liquid medium, e.g., buffers, to contain, e.g., suspend, the cellular components described above. In these instances, the control composition may be present in an amount ranging from 0.1 ml to 200 ml. For instance, the control composition may be present in an amount ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml.

The control composition may be stored at any suitable temperature. In some cases, the control composition is stored at temperatures ranging from 1° C. to 30° C., from 2° C. to 27° C., or from 5° C. to 25° C.

The control composition may be present in any suitable container that is compatible with the control composition. By "compatible" is meant that the container is substantially inert (e.g., does not significantly react with) the liquid and/or reagent(s) of the control composition in contact with a surface of the container. Containers of interest may vary and may include but are not limited to a blood collection tube, test tube, centrifuge tube, culture tube, falcon tube, microtube, Eppendorf tube, specimen collection container, specimen transport container, and syringe.

The container for holding the control composition may be configured to hold any suitable volume of the control composition. In some cases, the size of the container may depend on the volume of control composition to be held in the container. In certain embodiments, the container may be configured to hold an amount of control composition ranging from 0.1 mg to 1000 mg, such as from 0.1 mg to 900 mg, such as from 0.1 mg to 800 mg, such as from 0.1 mg to 700 mg, such as from 0.1 mg to 600 mg, such as from 0.1 mg to 500 mg, such as from 0.1 mg to 400 mg, or 0.1 mg to 300 mg, or 0.1 mg to 200 mg, or 0.1 mg to 100 mg, 0.1 mg to 90 mg, or 0.1 mg to 80 mg, or 0.1 mg to 70 mg, or 0.1 mg to 60 mg, or 0.1 mg to 50 mg, or 0.1 mg to 40 mg, or 0.1 mg to 30 mg, or 0.1 mg to 25 mg, or 0.1 mg to 20 mg, or 0.1 mg to 15 mg, or 0.1 mg to 10 mg, or 0.1 mg to 5 mg, or 0.1 mg to 1 mg, or 0.1 mg to 0.5 mg. In certain embodiments, the container is configured to hold an amount of control composition ranging from 0.1 g to 10 g, or 0.1 g to 5 g, or 0.1 g to 1 g, or 0.1 g to 0.5 g. In certain instances, the container is configured to hold a volume (e.g., a volume of a liquid control composition) ranging from 0.1 ml to 200 ml. For instance, the container may be configured to hold a volume (e.g., a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml. In certain instances, the container is configured to hold a volume (e.g., a volume of a liquid control composition) ranging from 0.1 ml to 200 ml.

The shape of the container may also vary. For example, the container including the control composition may find use in an assay, such as an flow cytometric assay. In these cases, the container may be configured in a shape that is compatible with the assay and/or the method or other devices used to perform the assay. For instance, the container may be configured in a shape of typical laboratory equipment used to perform the assay or in a shape that is compatible with other devices used to perform the assay. In some embodiments, the liquid container may be a vial or a test tube. In certain cases, the liquid container is a vial. In certain cases, the liquid container is a test tube.

As described above, embodiments of the container can be compatible with the control composition in contact with the reagent device. Examples of suitable materials for the containers include, but are not limited to, glass and plastic. For example, the container may be composed of glass, such as, but not limited to, silicate glass, borosilicate glass, sodium borosilicate glass (e.g., PYREX™), fused quartz glass, fused silica glass, and the like. Other examples of suitable materials for the containers include plastics, such as, but not limited to, polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), and the like.

In some embodiments, the container may be sealed. That is, the container may include a seal that substantially prevents the contents of the container from exiting the container. The seal of the container may also substantially prevent other substances from entering the container. For example, the seal may be a water-tight seal that substantially prevents liquids from entering or exiting the container, or may be an air-tight seal that substantially prevents gases from entering or exiting the container. In some instances, the seal is a removable or breakable seal, such that the contents of the container may be exposed to the surrounding environment when so desired, e.g., if it is desired to remove a portion of the contents of the container. In some instances, the seal is made of a resilient material to provide a barrier (e.g., a water-tight and/or air-tight seal) for retaining a sample in the container. Particular types of seals include, but are not limited to, films, such as polymer films, caps, etc., depending on the type of container. Suitable materials for the seal include, for example, rubber or polymer seals, such as, but not limited to, silicone rubber, natural rubber, styrene butadiene rubber, ethylene-propylene copolymers, polychloroprene, polyacrylate, polybutadiene, polyurethane, styrene butadiene, and the like, and combinations thereof. For example, in certain embodiments, the seal is a septum pierceable by a needle, syringe, or cannula. The seal may also provide convenient access to a sample in the container, as well as a protective barrier that overlies the opening of the container. In some instances, the seal is a removable seal, such as a threaded or snap-on cap or other suitable sealing element that can be applied to the opening of the container. For instance, a threaded cap can be screwed over the opening before or after a sample has been added to the container.

Methods of Use

Aspects of the embodiments of the invention also include using control compositions, e.g., as described above, as a controls, e.g. positive controls, in a marker detection assay. By "marker detection assay" is meant an assay for detecting the presence and/or absence of one or more markers in a composition. The methods may include performing a flow cytometric assay with the control composition. By "flow cytometric assay" is meant an analytical technique in which physical and/or chemical properties of particles are measured as they flow in a fluid sample through an investigation cuvette, commonly referred to as a flow cell. The fluid sample may be investigated by subjecting the fluid sample to a variety of stimuli, where light is one common stimulus technique. Devices containing a flow cell, and associated fluid flow, light delivery and light detection components, are typically referred to as flow cytometers. The flow cytometric assay may include focusing a test composition into a single particle stream which passes through a light source, during which scattered and emitted light from the particles is measured by various detectors. The measurements are used to generate multi-parameter data sets describing the physical characteristics of the particles and, if the particles are fluorescently labeled, their fluorescent properties. In some cases, the particles are labeled with a plurality of labeled binding members where each distinct label, e.g., fluorescent label, corresponds to a distinct marker. In certain aspects, the control composition serves as a positive control in the flow cytometric assay to validate the performance of a flow cytometric assay. The control composition may provide various markers (e.g., positive control markers of interest), as described above, for flow cytometric detection. In a given flow cytometric assay, each of a test composition and a control composition may be subjected to the flow cytometric assay and flow cytometric data may be obtained for each one of the test composition and the control composition. In certain embodiments, the methods include performing a flow cytometric assay with the control composition and/or the test composition according to any of the embodiments described herein, where the flow cytometric assay includes: contacting the control composition with one or more binding members specific to the one or more positive control markers to produce a labeled control composition; and introducing the labeled control composition to a flow cytometer to generate flow cytometric data that indicates whether the one or more positive control markers were detected, wherein flow cytometric data indicating detection of the one or more positive markers validates the functionality of the flow cytometric assay and the one or more binding members.

Detection of positive control markers of interest in the control composition (e.g., positive flow cytometric data or positive flow cytometric results) may validate the functionality of the flow cytometric assay and the one or more binding members, e.g., may indicate the assay is being correctly performed and the systems and reagents are functioning properly. In certain embodiments, flow cytometric data showing the positive control markers were detected indicates that the methods of preparing the control composition and/or the test composition for flow cytometric analysis (e.g., labeling the control composition and/or test composition, introducing the control composition and/or test composition to the flow cytometer) were performed correctly. In certain embodiments, flow cytometric data showing the positive control markers were detected indicates that the flow cytometric systems (e.g., the flow cytometer, computer software and hardware) were functioning properly and that setup of the flow cytometric systems was properly performed. In certain embodiments, flow cytometric data showing the positive control markers were detected indicates that the reagents used in the flow cytometric assay (e.g., binding members conjugated to the detectible labels, buffers, etc.) were functioning properly. In some cases, positive flow cytometric data for the control composition verifies the flow cytometric data or results obtained for a test composition. In such cases, the positive flow cytometric results may confirm negative flow cytometric results obtained for the test composition are truly negative and not due to an error in the experimental procedure or equipment/reagent malfunction. Negative flow cytometric results for the test composition may include flow cytometric data indicating that one or more markers of interest in the test composition were not detected in the test composition. In certain embodiments, the one or more markers of interest in the test composition that were not detected correspond to the one or more positive control markers of interest that were detected.

Figure 2:
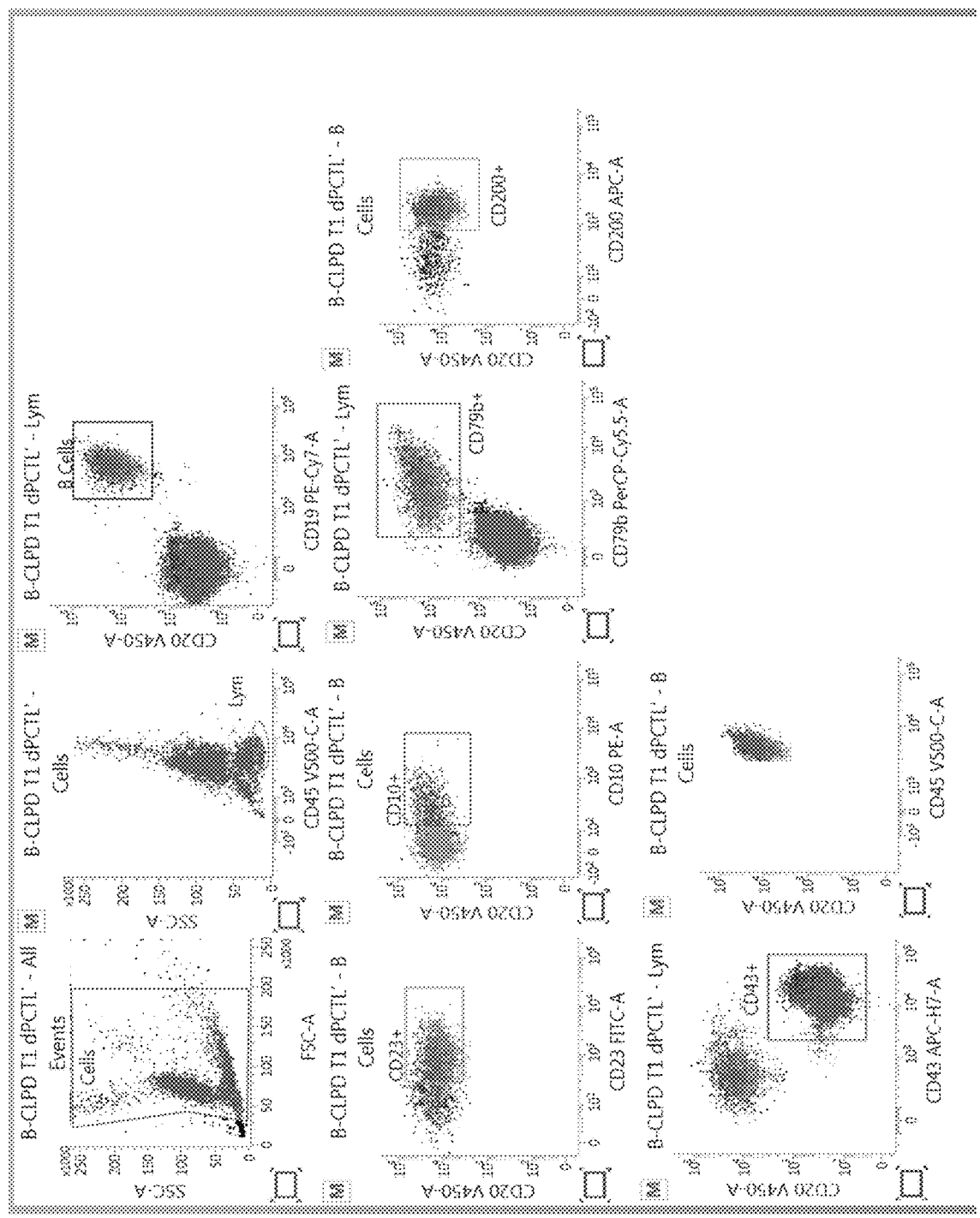
FIG. 2 provides results of a flow cytometric assay showing the detection of markers in a control composition labeled with BD OneFlow™ B-cell Chronic Lymphoproliferative Diseases Tube 1 (B-CLPD T1) antibody reagents and gating of cell populations expressing the detected markers.
Figure 3:
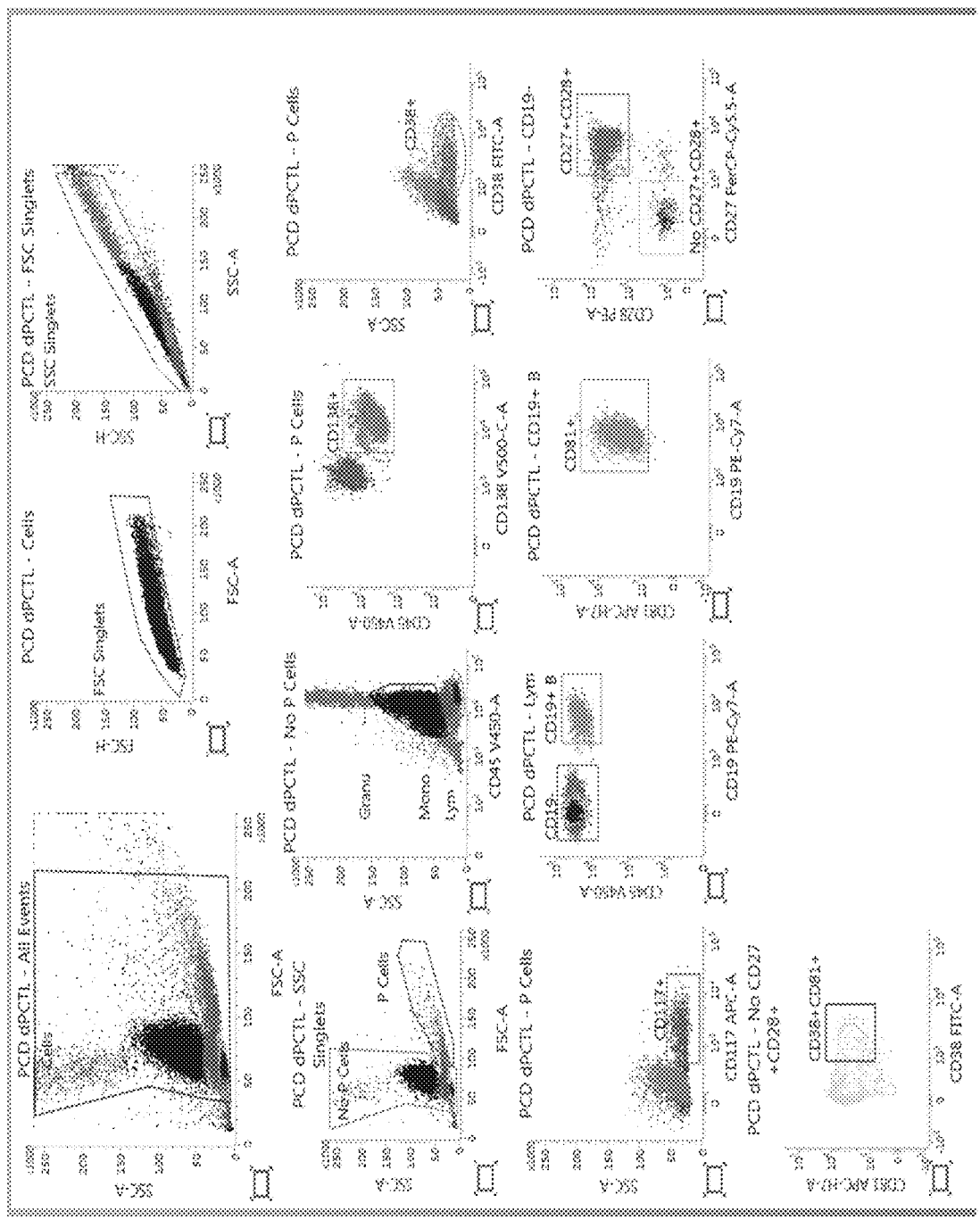
FIG. 3 provides results of a flow cytometric assay showing the detection of markers in a control composition labeled with BD OneFlow™ Plasma Cell Disorders (PCD) antibody reagents and gating of cell populations expressing the detected markers.
Figure 4:
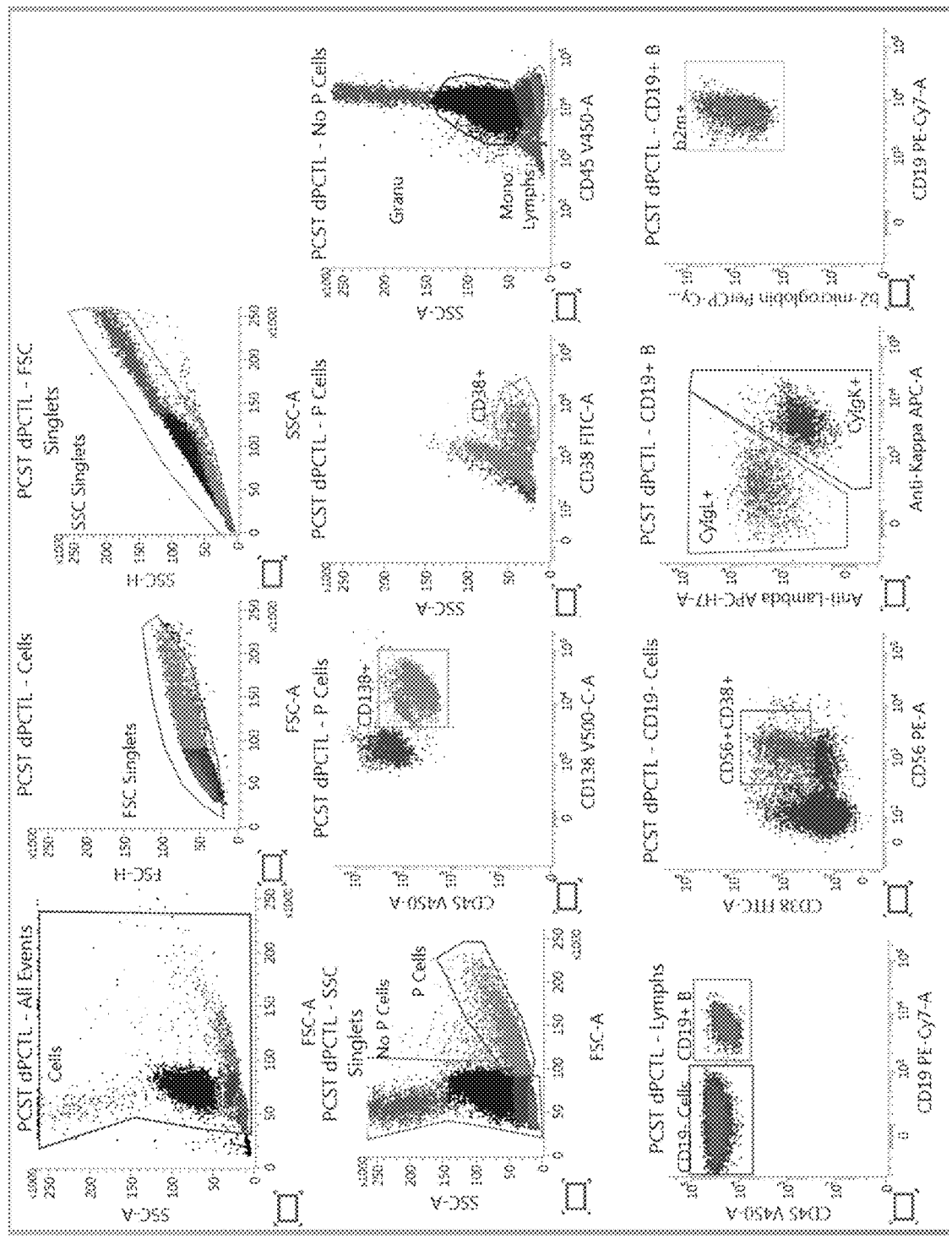
FIG. 4 provides results of a flow cytometric assay showing the detection of markers of in a control composition labeled with BD OneFlow™ Plasma Cell Screening Tube (PCST) antibody reagents and gating of cell populations expressing the detected markers.
Figure 5:
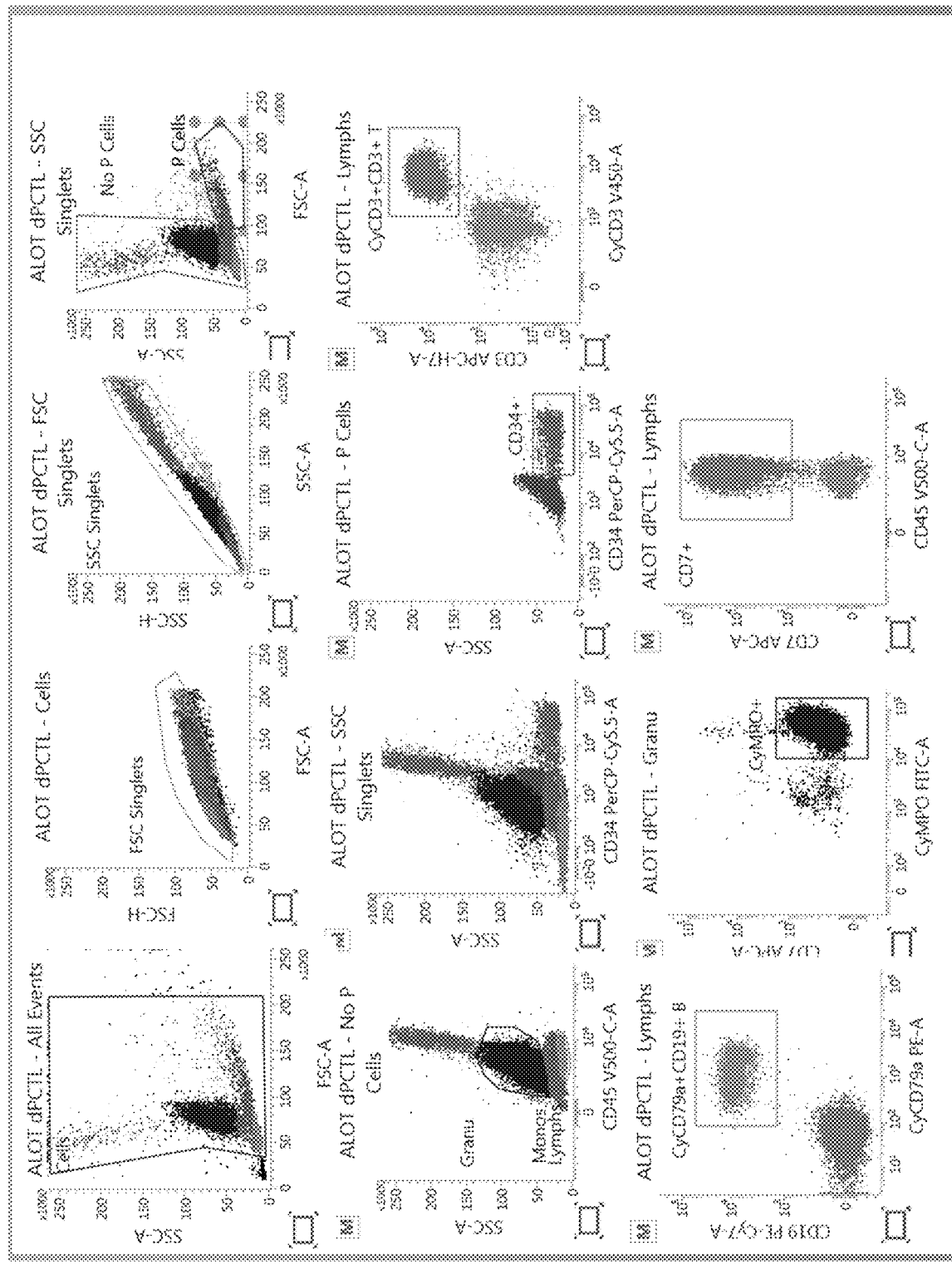
FIG. 5 provides results of a flow cytometric assay showing the detection of markers of in a control composition labeled with BD OneFlow™ Acute Leukemia Orientation Tube (ALOT) antibody reagents and gating of cell populations expressing the detected markers.
Figure 6:
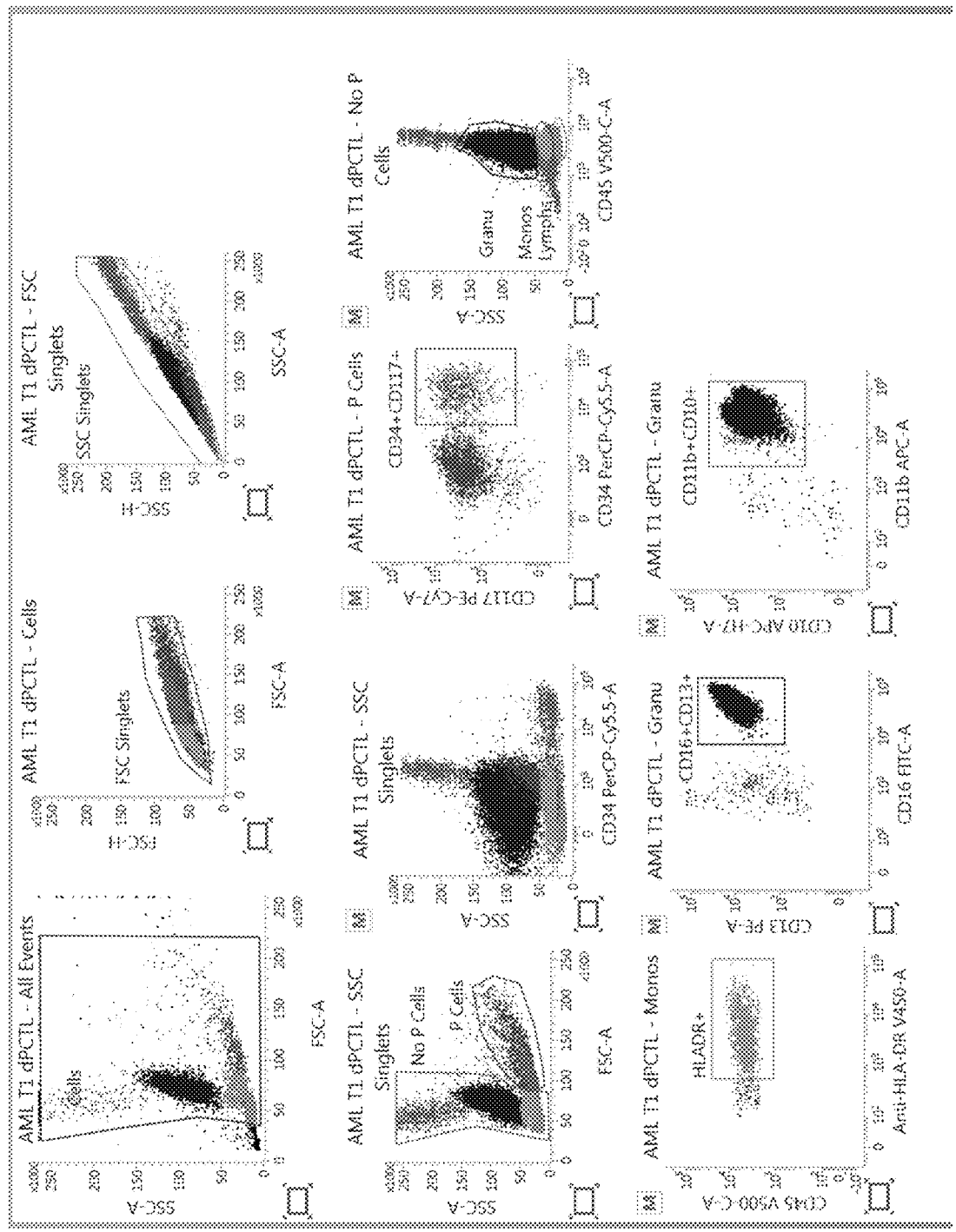
FIG. 6 provides results of a flow cytometric assay showing the detection of markers of acute myeloid leukemia type 1 (AML T1) in a control composition labeled with BD OneFlow™ ALOT reagents and gating of cell populations expressing the detected markers.
Figure 7:
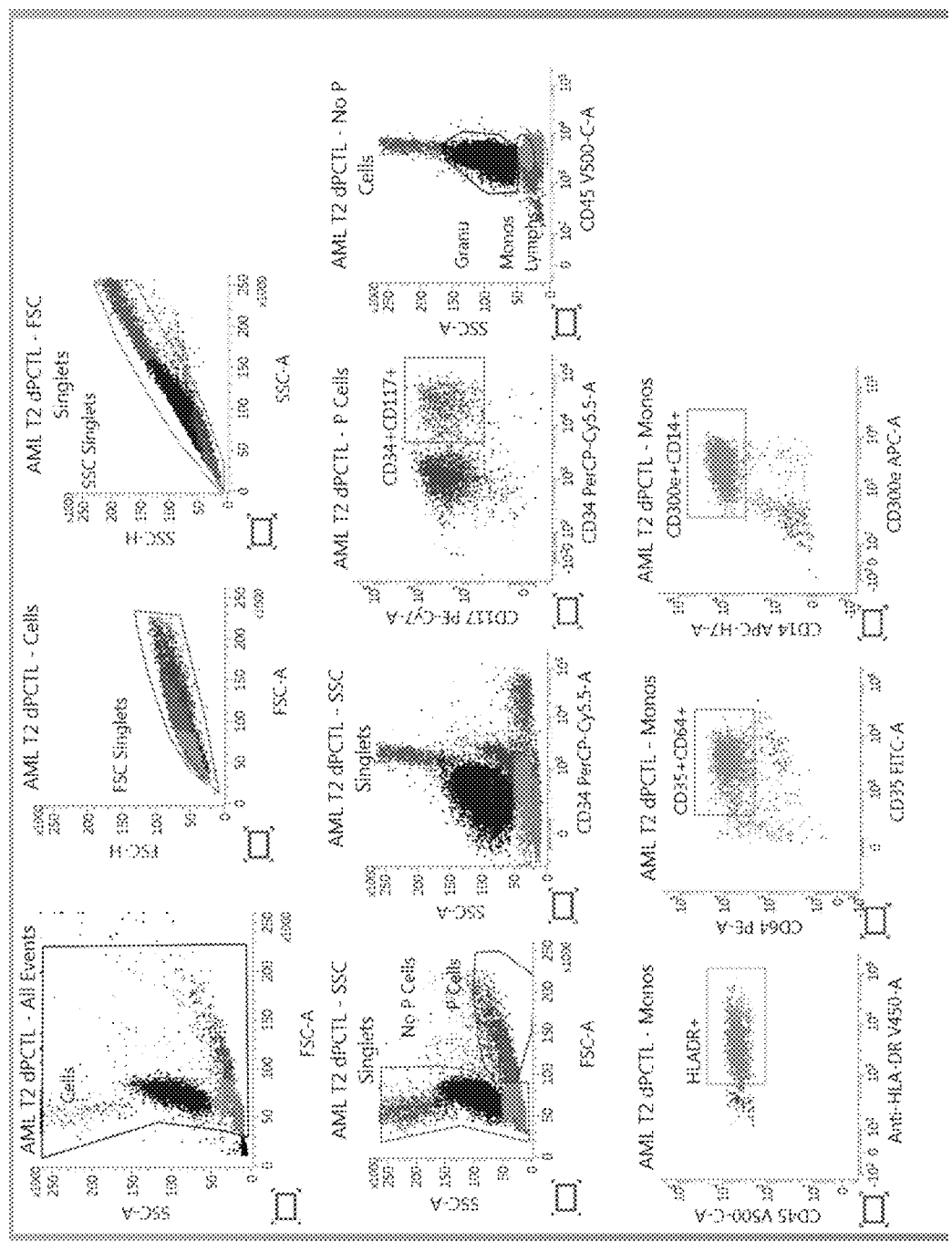
FIG. 7 provides results of a flow cytometric assay showing the detection of markers of acute myeloid leukemia type 2 (AML T2) in a control composition labeled with BD OneFlow™ ALOT reagents and gating of cell populations expressing the detected markers.
Figure 8:
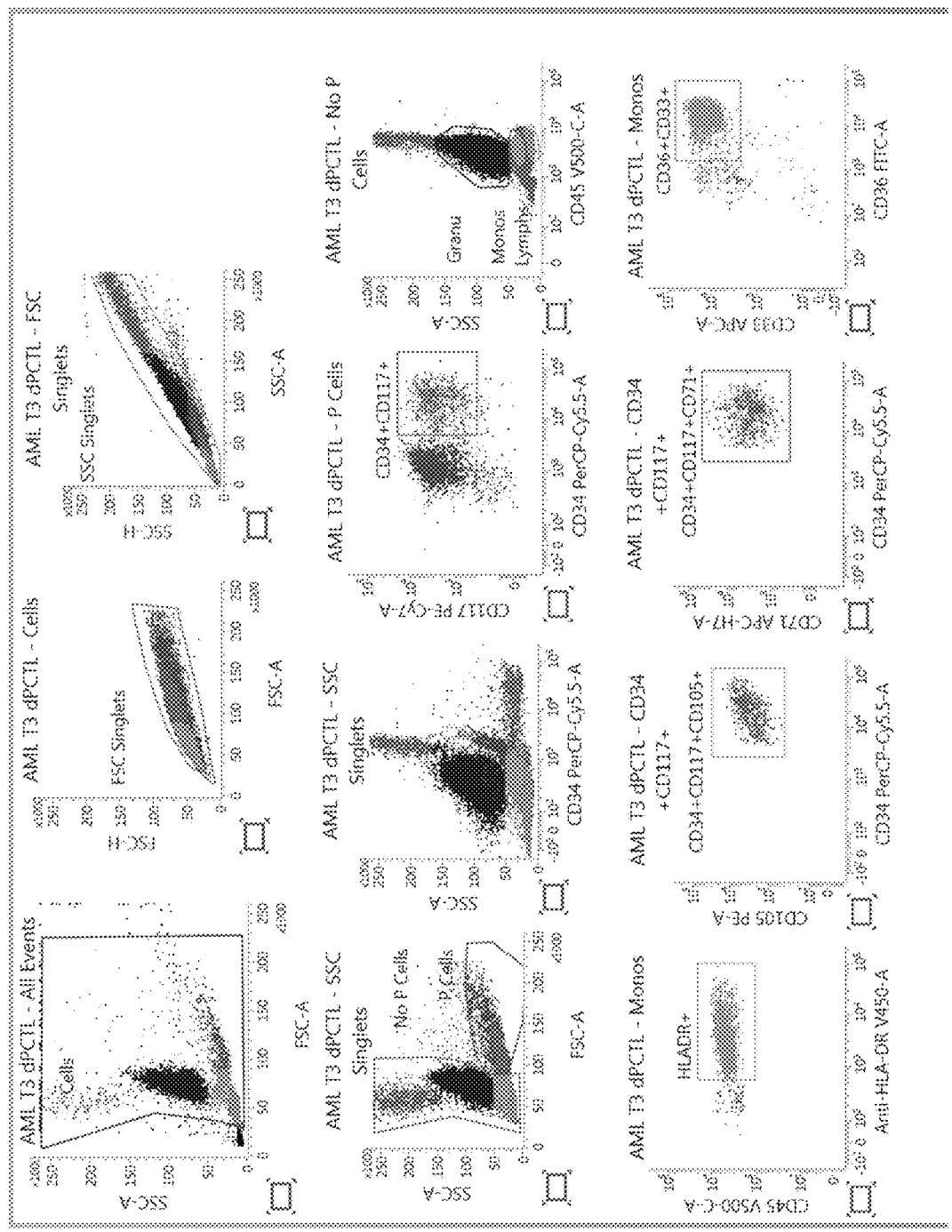
FIG. 8 provides results of a flow cytometric assay showing the detection of markers of acute myeloid leukemia type 3 (AML T3) in a control composition labeled with BD OneFlow™ ALOT reagents and gating of cell populations expressing the detected markers.
Figure 9:
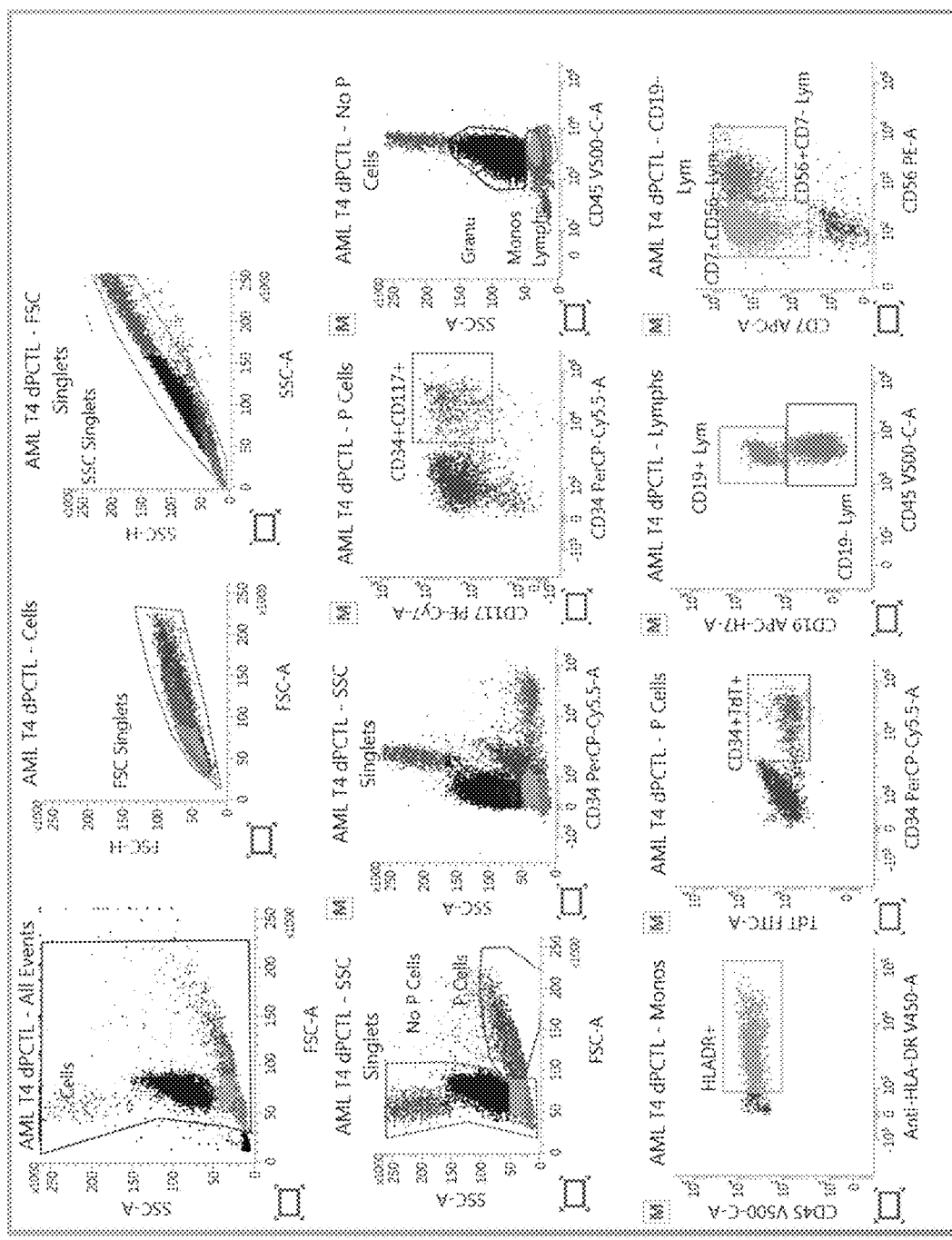
FIG. 9 provides results of a flow cytometric assay showing the detection of markers of acute myeloid leukemia type 4 (AML T4) in a control composition labeled with BD OneFlow™ ALOT reagents and gating of cell populations expressing the detected markers.
Figure 10:
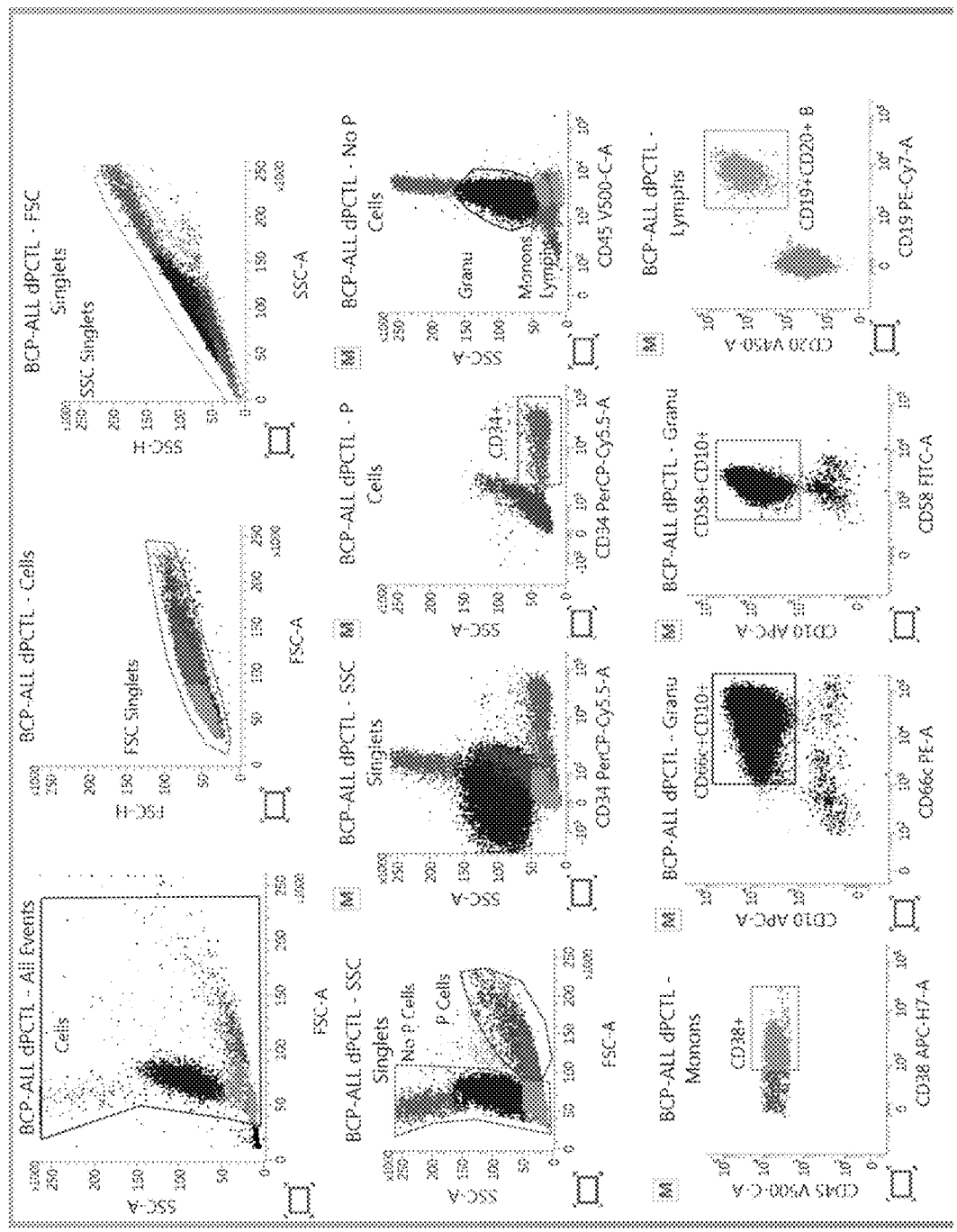
FIG. 10 provides results of a flow cytometric assay showing the detection of markers of B-cell precursor acute lymphoblastic leukemia (BCP-ALL) in a control composition labeled with BD OneFlow™ ALOT reagents and gating of cell populations expressing the detected markers.

Flow cytometric data can be provided as dot plots displaying two measurement parameters on the x-axis and y-axis respectively and events representing single detected particles. Exemplary plots are provided in FIGS. 1-10. In FIGS. 1-10, the parameters include fluorescence, forward scatter (FSC), and/or side scatter (SSC). Gates are placed around populations of cells with common characteristics, e.g., forward scatter, side scatter, and marker expression, to analyze and quantify these populations of interest. The populations of interest may be distinguished by their forward scatter and side scatter properties as well as their marker expression pattern as detected by fluorescence. Analysis of the dot plots allows for the identification of populations of normal and neoplastic cells. FIG. 1 provides flow cytometric data showing the detection of one or more positive control markers in a control composition labeled with BD OneFlow™ Lymphoid Screening Tube (LST) antibody reagents and gating of populations of cells expressing the one or more positive control markers. FIG. 2 provides flow cytometric data showing the detection of one or more positive control markers in a control composition labeled with BD OneFlow™ B-cell Chronic Lymphoproliferative Diseases Tube 1 (B-CLPD T1) antibody reagents and gating of populations of cells expressing the one or more positive control markers. FIG. 3 provides flow cytometric data showing the detection of one or more positive control markers in a control composition labeled with BD OneFlow™ Plasma Cell Disorders (PCD) antibody reagents and gating of populations of cells expressing the one or more positive control markers. FIG. 4 provides flow cytometric data showing the detection of one or more positive control markers in a control composition labeled with BD OneFlow™ Plasma Cell Screening Tube (PCST) antibody reagents and gating of populations of cells expressing the one or more positive control markers. FIG. 5 provides flow cytometric data showing the detection of one or more positive control markers in a control composition labeled with BD OneFlow™ Acute Leukemia Orientation Tube (ALOT) antibody reagents and gating of populations of cells expressing the one or more positive control markers. FIG. 6 provides flow cytometric data showing the detection of one or more positive control markers in a control composition for identifying acute myeloid leukemia type 1 (AML T1), wherein the control composition is labeled with BD OneFlow™ ALOT antibody reagents. FIG. 7 provides flow cytometric data showing the detection of one or more positive control markers in a control composition for identifying acute myeloid leukemia type 2 (AML T2), wherein the control composition is labeled with BD OneFlow™ ALOT antibody reagents. FIG. 8 provides flow cytometric data showing the detection of one or more positive control markers in a control composition for identifying acute myeloid leukemia type 3 (AML T3), wherein the control composition is labeled with BD OneFlow™ ALOT antibody reagents. FIG. 9 provides flow cytometric data showing the detection of one or more positive control markers in a control composition for identifying acute myeloid leukemia type 4 (AML T4), wherein the control composition is labeled with BD OneFlow™ ALOT antibody reagents. FIG. 10 provides flow cytometric data showing the detection of one or more positive control markers in a control composition for identifying B-cell precursor acute lymphoblastic leukemia (BCP-ALL), wherein the control composition is labeled with BD OneFlow™ ALOT antibody reagents.

Data showing detection of positive control markers of interest in the control composition did not occur may indicate the flow cytometric assay is being incorrectly performed and/or the systems and/or reagents are not functioning properly. In some cases, flow cytometric data showing the positive control markers were not detected reveals that the flow cytometric data obtained for a test composition is inaccurate and unreliable and that one or more of the steps and components of the flow cytometric assay performed on the test composition are compromised or not functioning correctly. In certain embodiments, flow cytometric data showing the positive control markers were not detected indicates that the methods of preparing the control composition and/or test composition for flow cytometric analysis (e.g., labeling the control composition and/or test composition, introducing the control composition and/or test composition to the flow cytometer) were performed incorrectly. In certain embodiments, flow cytometric data showing the positive control markers were not detected indicates that the flow cytometric systems (e.g., any of the flow cytometer, computer software and hardware, etc.) were not functioning properly and/or that setup of the flow cytometric systems was improperly performed. In certain embodiments, flow cytometric data showing the positive control markers were not detected indicates that the reagents used in the flow cytometric assay (e.g., any of the binding members conjugated to the detectible labels, buffers, etc.) were not functioning properly. In some cases, the data reveals that steps of a flow cytometric protocol may have been skipped or performed in the incorrect order or a reagent may not have been added at the appropriate time or at all. The data may indicate that the flow cytometric systems and reagents are in need of repair or replacement. In some cases, the data indicates that one or more parameters of the flow cytometric assay (e.g., cell concentration, flow cytometer settings, cell staining, cell permeabilization, washing, reconstitution, etc.) need adjustment. In some cases, the method includes adjusting (e.g., increasing, decreasing, resetting, etc.) one or more parameters of the flow cytometric assay based on the flow cytometric data.

The test composition subjected to the flow cytometric assay may be a biological sample obtained from a subject such as, e.g., a cell suspension prepared from the tissues or fluid (e.g., blood) of a subject. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

As summarized above, the methods may include contacting the control composition with one or more binding members specific to one or more positive control markers to produce a labeled control composition. The contacting may stably associate a labeled binding member with a positive control marker. Methods of contacting the control composition with one or more specific binding members may include combining a control composition with the specific binding members in a container or reaction chamber. In some instance, the control composition is contacted with the one or more specific binding members for a time sufficient to label the markers of interest, such as, for example, 10 minutes to overnight, including 20 to 30 min. In some instances, methods of contacting the control composition with the one or more specific binding members include combining, e.g., incubating, mixing, etc., the control composition with the one or more specific binding members. In some instances, the contacting comprises introducing or placing the control composition in a container that includes the labeled binding members. The labeled specific binding members may be present in the container in any convenient form, e.g., a storage stable composition. In some instances, the contacting may occur at temperatures ranging from 20 to 27 degrees Celsius, such as 22 degrees Celsius. The contacting may occur at pH ranging from 6.0 to 9.0, such as pH 7.4.

The control composition may be contacted with the detectible labels at the same time or in succession. The control composition may be contacted with a sufficient amount of the detectible labels and for a period of time sufficient to allow binding of detectible labels to their specific targets. For example, the control composition may be contacted for between 5 minutes and several hours, such as between 30 minutes and 2 hours. The control composition may be maintained at any convenient temperature, e.g., between freezing and room temperature, during the contacting step. A washing step may then be performed, as desired, e.g., to remove any unbound detectible labels and other control composition components. Washing may be performed using any convenient protocol, such as by combining the reaction mixture with a suitable wash buffer (e.g., PBS, HEPES) and separating the cells from the fluid. A given washing protocol may include one or more distinct washing steps, as desired. Following any washing protocol, the cells may be re-suspended in a suitable liquid (e.g., the washing buffer or another buffer).

A binding member may include a specific binding domain and a label domain. The terms "specific binding," "specifically binds," and the like, refer to the preferential binding of a domain (e.g., one binding pair member to the other binding pair member of the same binding pair) relative to other molecules or moieties in a solution or reaction mixture. The specific binding domain may bind (e.g., covalently or non-covalently) to a specific epitope within the cell. In certain aspects, specific binding domain non-covalently binds to a target. In such instances, the specific binding domain association with the binding target (e.g., one or more positive control markers) may be characterized by a KD (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. A variety of different types of specific binding domains may be employed as the capture ligands. Specific binding domains of interest include, but are not limited to, antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

In some cases, the one or more binding members (or specific binding members) is conjugated to a detectible label to form, e.g., labeled binding members. The detectible label may be detectible based on, for example, fluorescence emission maxima, fluorescence polarization, fluorescence lifetime, light scatter, mass, molecular mass, or combinations thereof. In certain aspects, the detectible label may be a fluorophore (i.e., a fluorescent label, fluorescent dye, etc.). Fluorophores can be selected from any of the many dyes suitable for use in analytical applications (e.g., flow cytometry, imaging, etc.). A large number of dyes are commercially available from a variety of sources, such as, for example, Molecular Probes (Eugene, OR) and Exciton (Dayton, OH). Examples of fluorophores that may be incorporated into the microparticles include, but are not limited to, 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, OR) and Exciton (Dayton, OH).

In some instances, the fluorophore is polymeric dye. In some instances of the method, the polymeric dye includes a conjugated polymer. Conjugated polymers (CPs) are characterized by a delocalized electronic structure which includes a backbone of alternating unsaturated bonds (e.g., double and/or triple bonds) and saturated (e.g., single bonds) bonds, where π-electrons can move from one bond to the other. As such, the conjugated backbone may impart an extended linear structure on the polymeric dye, with limited bond angles between repeat units of the polymer. For example, proteins and nucleic acids, although also polymeric, in some cases do not form extended-rod structures but rather fold into higher-order three-dimensional shapes. In addition, CPs may form "rigid-rod" polymer backbones and experience a limited twist (e.g., torsion) angle between monomer repeat units along the polymer backbone chain. In some instances, the polymeric dye includes a CP that has a rigid rod structure. The structural characteristics of the polymeric dyes can have an effect on the fluorescence properties of the molecules.

Polymeric dyes of interest include, but are not limited to, those dyes described by Gaylord et al. in U.S. Publication Nos. 20040142344, 20080293164, 20080064042, 20100136702, 20110256549, 20110257374, 20120028828, 20120252986, 20130190193, 20160264737, 20160266131, 20180231530, 20180009990, 20180009989, and 20180163054, the disclosures of which are herein incorporated by reference in their entirety; and Gaylord et al., J. Am. Chem. Soc., 2001, 123 (26), pp 6417-6418; Feng et al., Chem. Soc. Rev., 2010, 39, 2411-2419; and Traina et al., J. Am. Chem. Soc., 2011, 133 (32), pp 12600-12607, the disclosures of which are herein incorporated by reference in their entirety.

The polymeric dye may have one or more desirable spectroscopic properties, such as a particular absorption maximum wavelength, a particular emission maximum wavelength, extinction coefficient, quantum yield, and the like (see e.g., Chattopadhyay et al., "Brilliant violet fluorophores: A new class of ultrabright fluorescent compounds for immunofluorescence experiments." Cytometry Part A, 81A (6), 456-466, 2012). In some embodiments, the polymeric dye has an absorption curve between 280 nm and 475 nm. In certain embodiments, the polymeric dye has an absorption maximum (excitation maximum) in the range 280 nm and 475 nm. In some embodiments, the polymeric dye absorbs incident light having a wavelength in the range between 280 nm and 475 nm. In some embodiments, the polymeric dye has an emission maximum wavelength ranging from 400 nm to 850 nm, such as 415 nm to 800 nm, where specific examples of emission maxima of interest include, but are not limited to: 421 nm, 510 nm, 570 nm, 602 nm, 650 nm, 711 nm and 786 nm. In some instances, the polymeric dye has an emission maximum wavelength in a range selected from the group consisting of 410 nm to 430 nm, 500 nm to 520 nm, 560 nm to 580 nm, 590 nm to 610 nm, 640 nm to 660 nm, 700 nm to 720 nm, and 775 nm to 795 nm. In certain embodiments, the polymeric dye has an emission maximum wavelength of 421 nm. In some instances, the polymeric dye has an emission maximum wavelength of 510 nm. In some cases, the polymeric dye has an emission maximum wavelength of 570 nm. In certain embodiments, the polymeric dye has an emission maximum wavelength of 602 nm. In some instances, the polymeric dye has an emission maximum wavelength of 650 nm. In certain cases, the polymeric dye has an emission maximum wavelength of 711 nm. In some embodiments, the polymeric dye has an emission maximum wavelength of 786 nm. In certain instances, the polymeric dye has an emission maximum wavelength of 421 nm±5 nm. In some embodiments, the polymeric dye has an emission maximum wavelength of 510 nm±5 nm. In certain instances, the polymeric dye has an emission maximum wavelength of 570 nm±5 nm. In some instances, the polymeric dye has an emission maximum wavelength of 602 nm±5 nm. In some embodiments, the polymeric dye has an emission maximum wavelength of 650 nm±5 nm. In certain instances, the polymeric dye has an emission maximum wavelength of 711 nm±5 nm. In some cases, the polymeric dye has an emission maximum wavelength of 786 nm±5 nm. In certain embodiments, the polymeric dye has an emission maximum selected from the group consisting of 421 nm, 510 nm, 570 nm, 602 nm, 650 nm, 711 nm and 786 nm.

Specific polymeric dyes that may be employed include, but are not limited to, BD Horizon Brilliant™ Dyes, such as BD Horizon Brilliant™ Violet Dyes (e.g., BV421, BV510, BV605, BV650, BV711, BV786); BD Horizon Brilliant™ Ultraviolet Dyes (e.g., BUV395, BUV496, BUV737, BUV805); and BD Horizon Brilliant™ Blue Dyes (e.g., BB515) (BD Biosciences, San Jose, CA).

The fluorescent label may be distinguishable based on fluorescence emission maxima, and optionally further based on light scatter or extinction.

In other aspects, the label domain may be a metal isotope detectible by mass spectroscopy, such as by the time of flight mass spectrometer used in mass cytometry, e.g., as described in international patent application serial no. PCT/US2012/020950 published as WO/2010/097070, the disclosure of which is herein incorporated by reference.

The labeled binding members contacted with the control composition are, in some instances, the same as those contacted with the test composition. In certain embodiments, the labeled binding members contacted with the control composition and the test composition are obtained from the same source, e.g., the same kit or the same container(s) in a given kit. In certain embodiments, the labeled binding members contacted with the control composition and the test composition are provided in a BD OneFlow™ kit or a combination of BD OneFlow™ kits, described in detail below.

In some instances, methods of the invention include contacting the control and test compositions with labeled binding members for use in flow-cytometric immunophenotyping of neoplastic immature populations of hematopoietic cells (lymphoid and nonlymphoid lineage) in bone marrow and peripheral blood as an aid in the diagnosis of acute lymphoblastic leukemia and non-lymphoid acute leukemia, e.g., as provided by the BD OneFlow™ ALOT, where in some instances the labeled binding members are specific to MPO, CD79a, CD34, CD19, CD7, CD3 (cytoplasmic), CD3 (cell surface), and CD45.

In some instances, methods of the invention include contacting the control and test compositions with labeled binding members for use in flow-cytometric immunophenotyping of normal and neoplastic mature lymphocyte populations of B, T, and NK cell lineages in peripheral blood, bone marrow, and lymph nodes, as an aid in diagnosis of hematological disorders, e.g., as provided with the BD OneFlow™ LST, where in some instances the labeled binding members are specific to CD45, CD19, CD20, Lambda light chain, Kappa light chain, CD38, CD3, CD4, CD8, CD5, TCRγδ, and CD56.

In some instances, methods of the invention include contacting the control and test compositions with labeled binding members for use in flow-cytometric immunophenotyping of B cells in peripheral blood and bone marrow as an aid in the diagnosis of chronic lymphocytic leukemia and other B-cell chronic lymphoproliferative diseases, e.g., as provided with the BD OneFlow™ B-CLPD T1, where in some instances the labeled binding members are specific to CD23, CD10, CD79b, CD19, CD200, CD43, CD20, and CD45.

In some instances, methods of the invention include contacting the control and test compositions with labeled binding members for use in flow-cytometric immunophenotyping of normal polyclonal and neoplastic plasma cell populations in bone marrow as an aid in the diagnosis of hematological disorders, e.g., as provided with the BD OneFlow™ PCST, where in some instances the labeled binding members are specific to CD38, CD56, β2-Microglobulin, CD19, Kappa light chain, Lambda light chain, CD45, and CD138.

In some instances, methods of the invention include contacting the control and test compositions with labeled binding members for use in flow-cytometric immunophenotyping of normal and neoplastic plasma cells in bone marrow as an aid in the diagnosis of multiple myeloma or other plasma cell disorders, e.g., as provided with the BD OneFlow™ PCD tube, where in some instances the labeled binding members are specific to CD38, CD28, CD27, CD19, CD117, CD81, CD45, and CD138.

Detecting positive control markers labeled with detectible labels (i.e., first, second, and/or additional detectible labels) may include distinguishing the detectible labels based on fluorescence emission maxima. For example, fluorescence compensation between two or more detectible labels with spectral overlap may be employed to distinguish the signal (e.g., fluorescence emission) resulting from each of the detectible labels. Two or more detectible labels may also be distinguished based on light scattering, fluorescence lifetime, excitation spectra, or combinations thereof.

As summarized above, aspects of the methods may include introducing the labeled control composition into a flow cytometer to generate flow cytometric data that indicates whether the one or more positive control markers were detected. The positive control markers of a labeled control composition may be detected by flow cytometry. Flow cytometry is a methodology using multi-parameter data for identifying and distinguishing between different particles, such as cells or beads, that vary from one another (e.g., in terms of label, size, granularity, etc.) in a fluid medium. In flow cytometrically analyzing the particles (e.g., the cells prepared as described above), a liquid medium comprising the particles is first introduced into the flow path of the flow cytometer. When in the flow path, the particles are passed substantially one at a time through one or more sensing regions, where each of the particles is exposed individually to a source of monochromatic light and measurements of light scatter parameters and/or fluorescent emissions as desired (e.g., two or more light scatter parameters and measurements of one or more fluorescent emissions) are separately recorded for each particle. The data recorded for each particle is analyzed in real time or stored in a data storage and analysis means, such as a computer, as desired. U.S. Pat. No. 4,284,412 describes the configuration and use of a typical flow cytometer equipped with a single light source while U.S. Pat. No. 4,727,020 describes the configuration and use of a flow cytometer equipped with two light sources. The disclosures of these patents are herein incorporated by reference. Flow cytometers having more than two light sources may also be employed.

More specifically, in a flow cytometer, the particles are passed, in suspension, substantially one at a time in a flow path through one or more sensing regions where in each region each particle is illuminated by an energy source. The energy source may include an illuminator that emits light of a single wavelength, such as that provided by a laser (e.g., He/Ne or argon) or a mercury arc lamp with appropriate filters. For example, light at 488 nm may be used as a wavelength of emission in a flow cytometer having a single sensing region. For flow cytometers that emit light at two distinct wavelengths, additional wavelengths of emission light may be employed, where specific wavelengths of interest include, but are not limited to: 535 nm, 635 nm, and the like.

In series with a sensing region, a detector module that includes one or more detectors, e.g., light collectors, such as photomultiplier tubes (or "PMT"), is used to record light that passes through each particle (generally referred to as forward light scatter), light that is reflected orthogonal to the direction of the flow of the particles through the sensing region (generally referred to as orthogonal or side light scatter) and fluorescent light emitted from the particles, if it is labeled with fluorescent marker(s), as the particle passes through the sensing region and is illuminated by the energy source. Each of forward light scatter (or FSC), orthogonal light scatter (SSC), and fluorescence emissions comprise a separate parameter for each particle (i.e. each "event"). Thus, for example, two, three, four or more parameters can be collected (and recorded) from a particle labeled with two different fluorescence markers.

Accordingly, in flow cytometrically assaying the particles, the particles which may include different amounts of the first, second, and/or additional detectable labels are detected and uniquely identified by exposing the particles to excitation light and measuring the fluorescence of each particle in one or more detection channels, as desired. The excitation light may be from one or more light sources and may be either narrow or broadband. Examples of excitation light sources include lasers, light emitting diodes, and arc lamps. Fluorescence emitted in detection channels used to identify the particles and binding complexes associated therewith may be measured following excitation with a single light source, or may be measured separately following excitation with distinct light sources. If separate excitation light sources are used to excite the particle labels, the labels may be selected such that all the labels are excitable by each of the excitation light sources used.

Flow cytometers further include data acquisition, analysis and recording means, such as a computer, wherein multiple data channels record data from each detector for the light scatter and fluorescence emitted by each particle as it passes through the sensing region. The purpose of the analysis system is to classify and count particles wherein each particle presents itself as a set of digitized parameter values. In flow cytometrically assaying particles in methods of the invention, the flow cytometer may be set to trigger on a selected parameter in order to distinguish the particles of interest from background and noise. "Trigger" refers to a preset threshold for detection of a parameter. It is typically used as a means for detecting passage of particle through the laser beam. Detection of an event which exceeds the preset threshold for the selected parameter triggers acquisition of light scatter and fluorescence data for the particle. Data is not acquired for particles or other components in the medium being assayed which cause a response below the threshold. The trigger parameter may be the detection of forward scattered light caused by passage of a particle through the light beam. The flow cytometer then detects and collects the light scatter and fluorescence data for particle.

A particular subpopulation of interest may be further analyzed by "gating" based on the data collected for the entire sample. To select an appropriate gate, the data is plotted so as to obtain the best separation of subpopulations possible. This procedure is typically done by plotting forward light scatter (FSC) vs. side (i.e., orthogonal) light scatter (SSC) on a two dimensional dot plot. The flow cytometer operator then selects the desired subpopulation of particles (i.e., those cells within the gate) and excludes particles which are not within the gate. Where desired, the operator may select the gate by drawing a line around the desired subpopulation using a cursor on a computer screen. Only those particles within the gate are then further analyzed by plotting the other parameters for these particles, such as fluorescence. Gating based on fluorescence may then be used to further separate subpopulations of cells.

Where flow cytometric analysis is performed, any convenient flow cytometry system may be employed. In certain instances, flow cytometry systems of interest include BD Biosciences FACSCanto™ and FACSCanto II™ flow cytometers, BD Biosciences FACSVantage™, BD Biosciences FACSort™, BD Biosciences FACSCount™, BD Biosciences FACScan™, and BD Biosciences FACSCalibur™ systems, BD Biosciences Influx™ cell sorter, BD Biosciences Accuri™ C6 flow cytometer; BD Biosciences LSRFortessa™ flow cytometer, BD Biosciences LSRFortessa™ X-20 flow cytometer, BD Biosciences FACSVerse™ flow cytometer, BD Biosciences FACSAria™ III and BD FACSAria™ Fusion flow cytometers, BD Biosciences FACSJazz™ flow cytometer, or the like. In certain embodiments, the subject systems are flow cytometric systems, such those described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosure of which are herein incorporated by reference in their entirety.

In certain embodiments, the methods include performing any of the steps disclosed herein on a dried control composition, where the methods further include reconstituting the dried control composition. Reconstitution involves restoring the control composition, previously dried for preservation and storage, to a liquid form. The dried control composition may be reconstituted with buffer before contacting the dried control composition with detectible binding members and introducing the control composition to a flow cytometer. The control composition may be contacted with any suitable reconstituting agent such as, e.g., drying matrix buffer, in accordance with any convenient protocol to reconstitute the control composition. Reconstitution time may vary, and in some instances ranges from 1 minute to 30 minutes, such as from 5 minutes to 10 minutes. The temperature at which reconstitution takes place may vary, and in some instances the temperature may range from 0° C. to 50° C.

In some cases, the flow cytometric assay further comprises contacting the control composition with a permeabilizing agent. Permeabilization may allow binding agents, e.g., labeled binding members, to enter cells in the control composition and specifically bind to intracellular markers. Permeabilization may take place before contacting the control composition with binding members specific to positive control markers, as previously described. Permeabilization may take place after reconstituting a dried control composition, as previously described. The cells of the control composition may be permeabilized through exposure to any of a number of cell permeabilizing agents, such as methanol, acetone or a detergent (e.g., Triton™, NP-40, saponin, Tween® 20, digitonin, Leucoperm™, etc.), or a combination thereof. Permeabilization time may vary, and in some instances ranges from 1 minute to 1 hour, such as from 5 minutes to 30 minutes. The temperature at which permeabilization takes place may vary, and in some instances the temperature may range from 0° C. to 50° C.

Aspects of the methods may also include sorting particles of a sample, such as cells in a test composition or a control composition. Methods according to certain embodiments include irradiating a sample containing particles in a flow stream in an interrogation region of a flow cell, such as a flow cell of a particle sorting module, detecting light (e.g., fluorescent light) from the sample, and sorting the particles of the sample into a collection system. In certain embodiments, the sample is a biological sample and methods include sorting and collecting at least one type of cell.

Cells of interest may be targeted for separation from the flow stream according to a variety of parameters, such as a phenotypic characteristic identified via the attachment of a particular fluorescent label to cells of interest. In some embodiments, the system is configured to deflect analyzed droplets that are determined to include a target cell. A variety of cells may be targeted for sorting. Target cells of interest include, but are not limited to, stem cells, T cells, dendritic cells, B Cells, granulocytes, leukemia cells, lymphoma cells, NK cells, macrophages, monocytes, etc. Target cells of interest include cells that have a convenient marker or antigen that may be captured or labelled by a convenient affinity agent or conjugate thereof. For example, the target cell may include one or more antigens selected from MPO, CD79a, CD34, CD19, CD7, cytoplasmic and/or cell surface CD3, CD45, CD20, Lambda light chain, Kappa light chain, CD38, CD4, CD8, CD5, TCRγδ, CD56, CD23, CD10, CD79b, CD200, CD43, 132-Microglobulin, CD138, CD28, CD27, CD117, CD81, CD71, CD105, TdT.

In practicing methods of certain embodiments, an amount of an initial fluidic sample is injected into the flow cytometer. The amount of sample injected into the particle sorting module may vary, for example, ranging from 0.001 mL to 1000 mL, such as from 0.005 mL to 900 mL, such as from 0.01 mL to 800 mL, such as from 0.05 mL to 700 mL, such as from 0.1 mL to 600 mL, such as from 0.5 mL to 500 mL, such as from 1 mL to 400 mL, such as from 2 mL to 300 mL and including from 5 mL to 100 mL of sample.

Methods according to certain embodiments may include counting and sorting labeled particles (e.g., target cells) in a sample. In practicing the subject methods, the fluidic sample including the particles is first introduced into a flow nozzle of the system. Upon exit from the flow nozzle, the particles are passed substantially one at a time through the sample interrogation region where each of the particles is irradiated to a source of light and measurements of light scatter parameters and, in some instances, fluorescent emissions as desired (e.g., two or more light scatter parameters and measurements of one or more fluorescent emissions) are separately recorded for each particle. The particles are passed in the flow stream substantially one at a time in a flow path through the sample interrogation region in the particle sorting module where each particle is illuminated by a light source. Depending on the properties of the flow stream being interrogated, 0.001 mm or more of the flow stream may be irradiated with light, such as 0.005 mm or more, such as 0.01 mm or more, such as 0.05 mm or more, such as 0.1 mm or more, such as 0.5 mm or more and including 1 mm or more of the flow stream may be irradiated with light.

In certain embodiments, methods include irradiating a planar cross-section of the flow stream in the sample interrogation region, such as with a laser (as described above). In other embodiments, methods include irradiating a predetermined length of the flow stream in the sample interrogation region, such as corresponding to the irradiation profile of a diffuse laser beam or lamp.

In certain embodiments, methods including irradiating the flow stream at or near the flow cell nozzle orifice. For example, methods may include irradiating the flow stream at a position about 0.001 mm or more from the nozzle orifice, such as 0.005 mm or more, such as 0.01 mm or more, such as 0.05 mm or more, such as 0.1 mm or more, such as 0.5 mm or more and including 1 mm or more from the nozzle orifice. In certain embodiments, methods include irradiating the flow stream immediately adjacent to the flow cell nozzle orifice.

In series with a sensing region, detectors, such as photomultiplier tubes (or "PMT"), are used to record light that passes through each particle (in certain cases referred to as forward light scatter), light that is reflected orthogonal to the direction of the flow of the particles through the sensing region (in some cases referred to as orthogonal or side light scatter) and fluorescent light emitted from the particles, if it is labeled with fluorescent marker(s), as the particle passes through the sensing region and is illuminated by the energy source. Each of forward light scatter (or FSC), orthogonal light scatter (SSC), and fluorescence emissions (FL1, FL2, etc.) include a separate parameter for each particle (or each "event"). Thus, for example, two, three or four parameters can be collected (and recorded) from a particle labeled with two different fluorescence markers.

Suitable light detecting protocols, include but are not limited to optical sensors or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, light from the irradiated flow stream at the sample interrogation region of the particle sorting module is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, light is measured with a charge-coupled device (CCD). Where the light from the irradiated flow stream at the sample interrogation region of the particle sorting module is measured with a CCD, the active detecting surface area of the CCD may vary, such as from 0.01 cm2 to 10 cm2, such as from 0.05 cm2 to 9 cm2, such as from, such as from 0.1 cm2 to 8 cm2, such as from 0.5 cm2 to 7 cm2 and including from 1 cm2 to 5 cm2.

The data recorded for each particle is analyzed in real time or stored in a data storage and analysis means, such as a computer, as desired. U.S. Pat. No. 4,284,412 describes the configuration and use of a flow cytometer of interest equipped with a single light source while U.S. Pat. No. 4,727,020 describes the configuration and use of a flow cytometer equipped with two light sources.

In certain embodiments, the particles are detected and uniquely identified by exposing the particles to excitation light and measuring the fluorescence of each particle in one or more detection channels, as desired. Fluorescence emitted in detection channels used to identify the particles and binding complexes associated therewith may be measured following excitation with a single light source, or may be measured separately following excitation with distinct light sources. If separate excitation light sources are used to excite the particle labels, the labels may be selected such that all the labels are excitable by each of the excitation light sources used.

Methods in certain embodiments also include data acquisition, analysis and recording, such as with a computer, wherein multiple data channels record data from each detector for the light scatter and fluorescence emitted by each particle as it passes through the sample interrogation region of the particle sorting module. In these embodiments, analysis includes classifying and counting particles such that each particle is present as a set of digitized parameter values. The subject systems may be set to trigger on a selected parameter in order to distinguish the particles of interest from background and noise. "Trigger" refers to a preset threshold for detection of a parameter and may be used as a means for detecting passage of a particle through the light source. Detection of an event that exceeds the threshold for the selected parameter triggers acquisition of light scatter and fluorescence data for the particle. Data is not acquired for particles or other components in the medium being assayed which cause a response below the threshold. The trigger parameter may be the detection of forward scattered light caused by passage of a particle through the light beam. The flow cytometer then detects and collects the light scatter and fluorescence data for the particle.

A particular subpopulation of interest is then further analyzed by "gating" based on the data collected for the entire population. To select an appropriate gate, the data is plotted so as to obtain the best separation of subpopulations possible. This procedure may be performed by plotting forward light scatter (FSC) vs. side (i.e., orthogonal) light scatter (SSC) on a two dimensional dot plot. A subpopulation of particles is then selected (i.e., those cells within the gate) and particles that are not within the gate are excluded. Where desired, the gate may be selected by drawing a line around the desired subpopulation using a cursor on a computer screen. Only those particles within the gate are then further analyzed by plotting the other parameters for these particles, such as fluorescence. Where desired, the above analysis may be configured to yield counts of the particles of interest in the sample.

In certain embodiments, the system operates to determine a timeslot during which one or more collection systems are aligned with the deflected droplet receiving location, e.g., the output of a sort block of the flow cytometer. In some instances, the deflection signal includes an initial deflection sub-signal and a final deflection sub-signal; and the system operates to produce the deflection signal by sending an initial deflection sub-signal at the beginning of the timeslot that configures the deflector to deflect an analyzed droplet, when present. In certain cases, methods include sending a final deflection sub-signal to the particle sorting module at the end of the timeslot that configures the deflector not to deflect an analyzed droplet. In some embodiments, methods include sending a final deflection sub-signal to the particle sorting module after a single analyzed droplet has been deflected during the timeslot, where the final deflection sub-signal configures the deflector not to deflect an analyzed droplet. Sorted particles, e.g., cells, of interest may be collected by a collection system.

Aspects of the methods may further include flow cytometer systems, where the flow cytometer systems include a sorting flow cytometer operatively coupled to a collection system. Flow-type particle sorting systems, such as sorting flow cytometers, are used to sort particles in a fluid sample based on at least one measured characteristic of the particles. In a flow-type particle sorting system, particles, such as molecules, analyte-bound beads, or individual cells, in a fluid suspension are passed in a stream by a detection region in which a sensor detects particles contained in the stream of the type to be sorted. The sensor, upon detecting a particle of the type to be sorted, triggers a sorting mechanism that selectively isolates the particle of interest.

Particle sensing typically is carried out by passing the fluid stream by a detection region in which the particles are exposed to irradiating light, from one or more lasers, and the light scattering and fluorescence properties of the particles are measured. Particles or components thereof can be labeled with fluorescent dyes to facilitate detection, and a multiplicity of different particles or components may be simultaneously detected by using spectrally distinct fluorescent dyes to label the different particles or components. Detection is carried out using one or more photosensors to facilitate the independent measurement of the fluorescence of each distinct fluorescent dye.

One type of flow-type particle sorting system is the electrostatic sorting type. In an electrostatic sorter, a fluid suspension is jetted from a nozzle and vibrated to break the stream into uniform discrete drops. The sorting mechanism includes a drop charging means connected to the stream to charge drops containing a particle of the type to be sorted with an electrical charge as it breaks off from the jet stream. The stream of drops is passed through a transverse electrostatic field established by a pair of oppositely charged deflection plates. Charged drops containing a particle of the type to be sorted are deflected in a direction and in an amount related to the polarity and magnitude of the drop charge and are collected in distinct collection receptacles. Uncharged drops are not deflected passing through the electrostatic field and are collected by a central receptacle.

Various aspects of sorting flow cytometers are described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference in their entirety. In some instances, the sorting flow cytometer is a Becton Dickinson cell sort, such as the BD Biosciences Influx™ cell sorter, BD Biosciences FACSAria™ III and BD FACSAria™ Fusion cell sorters, BD Biosciences FACSJazz™ cell sorter, the BD Biosciences FACSMelody™ cell sorter, and the like.

Methods of Making

Embodiments of the invention also include methods of producing a control composition, e.g., as described above. The methods may include combining a first white blood cellular component including one or more positive control markers for white blood cells with a second cellular component including one or more positive control markers for hematopoietic stem/progenitor cells and a third cellular component including one or more positive control markers for neoplastic cells to produce a combined cellular composition, and contacting the combined cellular composition with a fixing agent to produce a control composition.

In some cases, the first white blood cellular component may be produced by obtaining white blood cells from a sample of whole blood. The sample of whole blood may be obtained from any suitable source such as, e.g., a human, non-human primate, murine, or another suitable mammal. The method may include producing the first white blood cellular component by any convenient method to separate white blood cells or red blood cells from the whole blood.

Suitable methods include, but are not limited to, centrifugation, sedimentation combined with centrifugation, acoustophoresis, flow cytometric sorting, immunomagnetic cell separation, microfluidic techniques. In some cases, the method includes depleting a whole blood sample of red blood cells. The method may include contacting an amount of whole blood with a lysing agent for lysing red blood cells to produce the first white blood cellular component. The lysing agent may disrupt and lyse the red blood cells in the whole blood and leave the white blood cells. Lysing may take place prior to producing the combined cellular composition and may be performed according to any suitable protocol. Any suitable red blood cell lysing agent may be used including, e.g., BD Pharm Lyse™ lysing agent, and the like. The amount of whole blood may be contacted with the lysing agent for an amount of time ranging from 5 to 20 minutes, from 10 to 20 minutes, from 10 to 15 minutes, or from 5 to 10 minutes. The amount of whole blood may be contacted with the lysing agent at a temperature ranging from 10 to 30 degrees Celsius, from 20 to 30 degrees Celsius, from 20 to 25 degrees Celsius, from 10 to 25 degrees Celsius, or from 15 to 25 degrees Celsius.

The method may further include washing the first white blood cellular component. The washing step may be performed after contacting an amount of whole blood with a lysing agent, e.g., to remove lysed red blood cells and other components from the white blood cellular component. Washing may be performed using any convenient protocol, such as by combining the lysed whole blood with a suitable wash buffer (e.g., PBS, HEPES) and separating cells from the fluid. A given washing protocol may include one or more distinct washing steps, as desired. Following any washing protocol, the cells may be re-suspended in a suitable liquid (e.g., the washing buffer or another buffer).

The method may further include centrifuging the first white blood cellular component after washing the lysed whole blood. Centrifugation may separate components of whole blood such as, e.g., the plasma from the cellular portion, so that one of the separated components, e.g., the cellular portion, may be collected. In some cases, centrifugation is performed to separate and collect white blood cells from a whole blood sample. The centrifugation may be performed according to any convenient protocol. In certain embodiments, the first white blood cellular component may be centrifuged at a temperature ranging from 10 to 30 degrees Celsius, from 20 to 30 degrees Celsius, from 20 to 25 degrees Celsius, from 10 to 25 degrees Celsius, or from 15 to 25 degrees Celsius. In certain embodiments, the first white blood cellular component may be centrifuged for a period of time ranging from 1 minute to 30 minutes, e.g. from 1 minute to 5 minutes or from 5 minutes to ten minutes.

The method may further include quantifying an amount of cells present in the first white blood cellular component, e.g., before combining the first white blood cellular component with the second cellular component and the third cellular component. The amount of cells, e.g., white blood cells, present in the first white blood cellular component may range from $4 \times 10^7$ to $5 \times 10^7$ cells, from $4 \times 10^7$ to $6 \times 10^7$ cells, from $5 \times 10^7$ to $6 \times 10^7$ cells. The first white blood cellular component may include an amount of cells that ranges from 80% to 95%, from 85% to 95%, or from 90% to 95% of total cells of the control composition.

The second cellular component may include any population of cells or parts of cells that provide positive control markers for hematopoietic stem/progenitor cells, as described in detail above. In some case, the second cellular component includes hematopoietic stem/progenitor cells (e.g., bone marrow cells, cord blood cells, etc.). In some cases, the method further includes producing the second cellular component by obtaining hematopoietic stem/progenitor cells, e.g., from a cultured stem cell line. The cultured stem cell line may be maintained according to any suitable methods known in the art. The hematopoietic stem/progenitor cells may be cells derived from any suitable mammal such as, e.g., a human, non-human primate, murine, or another suitable mammal. The hematopoietic stem/progenitor cells may be obtained from a cell line derived from any one of the following: fetal tissues, cord blood, bone marrow, peripheral blood, or mobilized peripheral blood or may be derived ex vivo from other cells, such as embryonic stem cells, induced pluripotent stem cells (iPS cells) or adult pluripotent cells. In certain embodiments, the method further includes quantifying the amount of cells present in the second cellular component, e.g., before combining the second cellular component with the first white blood cellular component or the third cellular component. The second cellular component may include any suitable amount of cells ranging from $4 \times 10^6$ to $6 \times 10^6$ cells, from $4 \times 10^6$ to $5 \times 10^6$ cells, or from $5 \times 10^6$ to $6 \times 10^6$ cells. The amount of cells in the second cellular component may range from 1% to 10%, from 3% to 10%, or from 5% to 10% of total cells of the control composition.

The third cellular component may include any population of cells or parts of cells that provide positive control markers for neoplastic cells, as described in detail above. In some cases, the third cellular component includes neoplastic cells, as described in detail above, such as, e.g., lymphoma cells, leukemia cells, and/or myeloma cells. In some cases, the method further includes producing the third cellular component by obtaining neoplastic cells, e.g., from a cultured neoplastic cell line, e.g., a blood cancer cell line. The cultured neoplastic cell line may be maintained according to any suitable methods known in the art. The neoplastic cells may be cells derived from any suitable mammal such as, e.g., a human, non-human primate, murine, or another suitable mammal. In certain embodiments, the neoplastic cells are obtained from cell lines derived from peripheral blood, bone marrow, and lymph nodes. In certain embodiments, the method further includes quantifying the amount of cells present in the second cellular component, e.g., before producing the combined cellular composition. The third cellular component may include any suitable amount of cells ranging from $4 \times 10^6$ to $6 \times 10^6$ cells, from $4 \times 10^6$ to $5 \times 10^6$ cells, or from $5 \times 10^6$ to $6 \times 10^6$ cells. The amount of cells in the third cellular component may range from 1% to 10%, from 3% to 10%, or from 5% to 10% of total cells in the control composition.

Combining the first white blood cellular component, the second cellular component, and the third cellular component may be performed by contacting each of the cellular components with one another. In certain embodiments, combining the first white blood cellular component, the second cellular component, and the third cellular component may be performed by introducing each of the cellular components to a single container, i.e., the same container. In certain embodiments, combining the cellular components includes mixing or stirring the cellular components together in a container to form a homogenous mixture. In some cases, the cellular components are combined, e.g., mixed together, for an amount of time ranging from 5 to 20 minutes, from 10 to 20 minutes, from 10 to 15 minutes, or from 5 to 10 minutes. In certain embodiments, the combining may occur at a temperature ranging from 10 to 30 degrees Celsius, from 20 to 30 degrees Celsius, from 20 to 25 degrees Celsius, from 10 to 25 degrees Celsius, or from 15 to 25 degrees Celsius.

In certain embodiments, the method further includes fixing the cellular components to produce a control composition. The combined cellular composition or one or more of the first white blood cellular component, the second cellular component, and the third cellular component may be fixed through exposure to any of a number of cell fixing agents (i.e., fixation reagents), such as paraformaldehyde, glutaraldehyde, methanol, acetone, formalin, or any combination thereof. Other fixatives and fixation methods may be employed, as desired. Fixation time may vary, and in some instances ranges from 1 minute and 1 hour, such as, e.g., from 5 minutes and 30 minutes or from 30 minutes to an hour. The temperature at which fixation takes place may vary, and in some instances the temperature ranges from −30 degrees Celsius to 30 degrees Celsius, such as from 15 degrees Celsius to 25 degrees Celsius, from 10 degrees Celsius to 20 degrees Celsius, or from 20 degrees Celsius to 25 degrees Celsius.

The method may further include washing the control composition. The washing step may be performed after fixing, e.g., to remove excess reagent, debris, and other components from the control composition. Washing may be performed using any convenient protocol, such as by combining the control composition with a suitable wash buffer (e.g., PBS, HEPES) and separating cells from the fluid. A given washing protocol may include one or more distinct washing steps, as desired. Following any washing protocol, the cells may be re-suspended in a suitable liquid (e.g., the washing buffer or another buffer).

In some cases, the method further includes centrifuging the control composition according to any of the methods disclosed herein. Centrifugation of the control composition may occur after washing the cellular components of the control composition, e.g., to separate the combined cellular components from excess reagent (e.g., wash buffer).

In some cases, the method further includes reconstituting the control composition with buffer. The control composition may be reconstituted after washing and centrifuging the control composition. The control composition may be contacted with any suitable reconstituting agent such as, e.g., drying matrix buffer, in accordance with any convenient protocol. Reconstitution time may vary, and in some instances ranges from 1 minute to 30 minutes, such as from 5 minutes to 10 minutes. The temperature at which reconstitution takes place may vary, and in some instances the temperature may range from 0° C. to 50° C.

In some cases, the method further includes quantifying an amount of cells present in the control composition. The control composition may include any suitable number of cells. In some cases, the control composition includes an amount of cells ranging from $4 \times 10^7$ to $6 \times 10^7$ cells, from $5 \times 10^7$ to $6 \times 10^7$ cells, or from $5 \times 10^7$ to $7 \times 10^7$ cells. In some cases, the method further includes processing of the control composition after quantifying the amount of cells present in the control composition. In some cases, the method further includes centrifuging the control composition. In some cases, the method further includes reconstituting the control composition with buffer.

In some cases, the method further includes drying the control composition. The control composition may be dried according to any convenient protocol that stabilizes and allows storage of the control composition without affecting the functionality of the composition, e.g., without disrupting the markers present in the control composition. The control composition may be dried by, e.g., air drying, lyophilization, vacuum concentration evaporation, nitrogen blow-down evaporation, heating, etc. Drying time may vary, and in some instances ranges from 1 minute to 30 minutes, such as from 5 minutes to 10 minutes. The temperature at which drying takes place may vary, and in some instances the temperature may range from 0° C. to 50° C.

Utility

The composition, methods, and kits of the present disclosure find use in a variety of different applications where detection of markers in a positive control is desired. Such applications include quality control of flow cytometric assays and flow cytometric systems, methods, and reagents. In flow cytometric applications, a positive control may contribute to standardizing procedures for flow cytometer setup; determination of assay settings; sample preparation, staining, and acquisition; and data analysis. For example, the control composition may be used as a positive control in a flow cytometric assay, where detection of one or more markers known to be present in the control composition validates the performance of the flow cytometric assay, e.g., the flow cytometric methods and systems used therein. The control composition may also serve as a positive control for one or more reagents of a flow cytometric assay such as, e.g., antibodies conjugated to detectable labels. In some cases, suitable applications include microscopy and immunohistochemistry.

In certain embodiments, a control composition of the present disclosure serves as a positive control in a diagnostic or research-based application. Such applications may include, e.g., flow cytometric immunophenotyping of normal and neoplastic cells such as, e.g., normal or neoplastic populations of hematopoietic stem/progenitor cells (e.g., lymphoid and non-lymphoid lineage) and/or populations of leukocytes (e.g., B cells, plasma cells, T cells, and NK cells) in bone marrow, peripheral blood, and/or lymph node tissue. In some cases, diagnostic applications of interest include flow cytometric assays for identifying and classifying hematological disorders and for determining whether an individual has a hematological disorder such as, e.g., leukemia or lymphoma.

In some cases, the control compositions of the present disclosure serve as a positive control for all the markers detectable by a BD OneFlow™ panel of antibody reagents. In certain embodiments, the control composition is suitable for use as a positive control in a flow cytometric assay incorporating any of the BD OneFlow™ panels such as, e.g., the BD OneFlow™ Acute Leukemia Orientation Tube (ALOT), the BD OneFlow™ Lymphoid Screening Tube (LST), the BD OneFlow™ B-cell Chronic Lymphoproliferative Diseases Tube 1 (B-CLPD T1), the BD OneFlow™ Plasma Cell Screening Tube (PCST), and the BD OneFlow™ Plasma Cell Dyscrasia tube (PCD).

Kits

Also provided by the present disclosure are kits. The kits include one or more reagents useful in practicing the methods of the present disclosure. In certain aspects, the kits include a container including a control composition according to any of the embodiments described herein.

In some cases, the kit further includes one or more containers comprising one or more binding members specific to the one or more positive control markers, as described in detail above. The one or more binding members may be conjugated to a detectable label (e.g., a fluorescent label). In some cases, the one or more binding members includes an antibody.

The one or more containers may include one or more binding members suitable for detecting a combination of positive control markers of interest. In some cases, the one or more binding members, e.g, antibody reagents, are provided in a BD OneFlow™ kit or a combination of BD OneFlow™ kits. The BD OneFlow™ kits may provide fluorochrome-conjugated antibodies in a dried formulation, where each antibody specific to a given marker is conjugated to a unique fluorochrome. Each kit may contain a set of antibody reagents specific to backbone markers and a set of antibody reagents specific to classification markers. Backbone markers may be shared across a particular set of panels and may be used to normalize the samples so that data files can be combined and analyzed as a single large data file. Backbone markers may be markers that identify distinct populations in a particular cell linage. Classification markers may be used to discriminate between cell types within a given lineage and to classify the abnormal cell type in the sample.

In some instances, the one or more containers include labeled binding members for use in flow-cytometric immunophenotyping of neoplastic immature populations of hematopoietic cells (lymphoid and nonlymphoid lineage) in bone marrow and peripheral blood as an aid in the diagnosis of acute lymphoblastic leukemia and non-lymphoid acute leukemia, e.g., as provided by the BD OneFlow™ ALOT, where in some instances the labeled binding members are MPO, CD79a, CD34, CD19, CD7, CD3 (cytoplasmic), CD3 (cell surface), CD45. In some cases, the antibody reagents are provided in two single-use tubes: an (S) tube containing antibody reagents specific to cell surface markers and a (C) tube containing antibody reagents specific to cell surface markers. The cytoplasmic markers may include MPO, CD79a, and CD3. The cell surface markers may include CD34, CD19, CD7, CD3, and CD45. For a B-Cell Precursor Acute Lymphoblastic Leukemia (BCP-ALL) panel, the backbone markers in BD OneFlow ALOT may include CD45, CD34, and CD19. For a T-cell Acute Lymphoblastic Leukemia (T-ALL) panel, the backbone markers in BD OneFlow ALOT may include CD45, cytoplasmic CD3 (cyCD3), and CD3. For acute myeloid leukemia (AML) panels, the backbone markers in BD OneFlow ALOT may include CD45 and CD34. CD34 and negative or dim expression of CD45 (CD45neg/dim) may be used as markers for immature cells. Cytoplasmic myeloperoxidase (cyMPO) may be used a myeloid lineage marker. cyCD3 and CD7 may be used as T-cell lineage markers. CD3 may be used as a maturity marker for T cells. CD19 and cytoplasmic CD79a (cyCD79a) may be used as B-cell lineage markers.

In some instances, the one or more containers include labeled binding members for flow-cytometric immunophenotyping of normal and neoplastic mature lymphocyte populations of B, T, and NK cell lineages in peripheral blood, bone marrow, and lymph nodes, as an aid in diagnosis of hematological disorders, e.g., as provided with the BD OneFlow™ LST, where in some instances the labeled binding members are CD45, CD19, CD20, Lambda light chain, Kappa light chain, CD38, CD3, CD4, CD8, CD5, TCRγδ, and CD56. The BD OneFlow™ LST may provide a single-use tube containing the labeled binding members. In some cases, CD45 is used to identify mature lymphocytes and B-cell precursors. In some cases, CD3 is used to identify T cells. In some cases, CD3 is used to identify B cells and NK cells by exclusion. In some cases, Anti-TCRγ/δ-1, CD5, CD4, and CD8 are used to separate T cells into a number of subpopulations. In some cases, CD19 and CD20 are used to identify B cells, and together with CD45 can separate B cells into mature B lymphocytes (CD19+, CD20hi, CD45hi) and B-cell precursors (CD19+, CD20−/lo, CD45lo). In some cases, CD19 and CD20 are used to identify NK cells by exclusion. In some cases, Anti-Kappa and Anti-Lambda are used to identify normal and clonally expanded populations of B cells expressing Igκ or Igλ on the surface membrane, respectively. In some cases, CD38 are used to identify plasma cells and B-cell precursors. In some cases, CD38 is used in the evaluation of a lymphoid malignancies. In some cases, CD38 may be used to aid in the identification of NK cells. In some cases, CD56 is used to identify NK cells.

In some instances, the one or more containers include labeled binding members flow-cytometric immunophenotyping of B cells in peripheral blood and bone marrow as an aid in the diagnosis of chronic lymphocytic leukemia (CLL) and other B-cell chronic lymphoproliferative diseases, e.g., as provided with the BD OneFlow™ B-CLPD T1, where in some instances the labeled binding members are CD23, CD10, CD79b, CD19, CD200, CD43, CD20, and CD45. The BD OneFlow™ B-CLPD T1 may provide a single-use tube containing labeled binding members. In some cases, the BD OneFlow™ B-CLPD T1 may be used for specimens with B-lineage populations needing further investigation in combination with the BD OneFlow™ LST to distinguish CLL from other B-cell chronic lymphoproliferative diseases. In some cases, CD45, CD19, and CD20 are present in both BD OneFlow™ LST and BD OneFlow™ B-CLPD T1 and serve as backbone markers, allowing for the direct comparison of specimens stained using the two tubes. In some cases, CD23, CD200, CD79b, CD43, and CD10 are used as classification markers and, together with CD5 and CD38 from BD OneFlow™ LST, allow for specimens to be classified as CLL or as other B-cell chronic lymphoproliferative diseases. In some cases, Anti-Kappa and Anti-Lambda, present in BD OneFlow™ LST, assess the clonality of the B-cell population.

In some instances, the one or more containers include labeled binding members for flow-cytometric immunophenotyping of normal polyclonal and neoplastic plasma cell populations in bone marrow as an aid in the diagnosis of hematological disorders, e.g., as provided with the BD OneFlow™ PCST, where in some instances the labeled binding members are CD38, CD56, β2-Microglobulin, CD19, Kappa light chain, Lambda light chain, CD45, and CD138. In some cases, the labeled binding members are provided in two single-use tubes: an (S) tube containing labeled binding members specific to cell surface markers and a (C) tube containing labeled binding members specific to cell surface markers. The cell surface markers may include CD38, CD56, β2-Microglobulin, CD19, CD45, and CD138. The intracellular markers may include Kappa light chain and Lambda light chain. In some cases, CD38, CD138, CD45, and CD19 are used as backbone markers to identify plasma cells. In some cases, CD56 and β2-Microglobulin are used as classification markers to identify aberrant plasma cell populations. In some cases, Anti-Kappa and Anti-Lambda are used to assess the clonality of the plasma cells. In some cases, CD19, Anti-Kappa, and Anti-Lambda are used to identify and characterize mature B cells.

In some instances, the one or more containers include labeled binding members for use in flow-cytometric immunophenotyping of normal and neoplastic plasma cells in bone marrow as an aid in the diagnosis of multiple myeloma or other plasma cell disorders, e.g., as provided with the BD OneFlow™ PCD tube, where in some instances the labeled binding members are CD38, CD28, CD27, CD19, CD117, CD81, CD45, and CD138. The BD OneFlow™ PCD tube may provide a single-use tube containing labeled binding members. The BD OneFlow™ PCD tube may be utilized in parallel with the BD OneFlow™ PCST. In some cases, CD38, CD138, CD45, and CD19 are used as backbone markers to identify plasma cells. In some cases, CD27, CD28, CD117, and CD81 are used as classification markers to identify aberrant plasma cell populations.

The kit may further include reagents for performing a flow cytometric assay. Examples of said reagents include buffers for at least one of reconstitution and dilution of the detectible molecules, buffers for contacting the control composition or a cell sample with one or more of the binding members, wash buffers, control beads, fluorescent beads for flow cytometer calibration and combinations thereof.

The binding members and/or reagents described above may be provided in liquid or dry (e.g., lyophilized) form. Any of the above components (binding members and/or reagents) may be present in separate containers (e.g., separate tubes, bottles, or wells in a multi-well strip or plate). In addition, one or more components may be combined into a single container, e.g., a glass or plastic vial, tube or bottle.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the internet to access the information at a removed site. Any convenient means may be present in the kits.

The following examples are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

Example 1: Dry DCTL-CD34+CD138+ Composition with Spiking of Cultured CD34+ Cells and U266 Cells The following description provides an exemplary method for preparing a whole blood based positive control including all the markers/antigens in BD OneFlow™ panels from $5 \times 10^6$ cultured human BM (bone marrow) CD34+ cells (P1, D10), $5 \times 10^6$ U266 cells (in house QC culture group provided), and SDP (in house) containing $5.9 \times 10^7$ WBC before spiking. The positive control is prepared according to the following steps:

1. Lyse SDP with 1× Pharm Lyse (15 min, RT);
2. Wash, spin and count cells;
3. $5 \times 10^6$ cultured CD34+ cells and $5 \times 10^6$ U266 cells are spiked into $5.9 \times 10^7$ lysed WBC (7.2% spiking for both cells), another $1.5 \times 10^7$ lysed WBC without spiking;
4. Fix spiked and non-spiked WBC with 1% PFA (60 min, RT);
5. Wash, spin, reconstitute with 1× Drying Matrix Buffer then count cells;
6. Spin, then reconstitute $5.72 \times 10^7$ spiked WBC, $1.42 \times 10^7$ non-spiked WBC with 4× Drying Matrix Buffer;
7. Aliquot and Dry down 20 tubes of $2.86 \times 10^6$/tube of spiked WBC (dCTL-CD34+CD138+ lot1), and 5 tubes of $2.84 \times 10^6$/tube of non-spiked WBC (DLK).

Notwithstanding the appended claims, the disclosure is also defined by the following clauses:

1. A control composition comprising:
   a first white blood cellular component comprising one or more positive control markers for white blood cells;
   a second cellular component comprising one or more positive control markers for hematopoietic stem/progenitor cells; and
   a third cellular component comprising one or more positive control markers for neoplastic cells,
   wherein the first white blood cellular component, the second cellular component, and third cellular component are fixed.

2. The control composition of clause 1, wherein the one or more positive control markers comprise cell surface markers.

3. The control composition of any of clauses 1-2, wherein the one or more positive control markers comprise intracellular markers.

4. The control composition of any of clauses 1-3, wherein the control composition comprises 50% or more of the positive control markers selected from the group consisting of: MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

5. The control composition of any of clauses 1-4, wherein the control composition comprises 60% or more of the positive control markers selected from the group consisting of: MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

6. The control composition of any of clauses 1-5, wherein the control composition comprises 80% or more of the positive control markers selected from the group consisting of: MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

7. The control composition of any of clauses 1-6, wherein the control composition comprises the following positive control markers: MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

8. The control composition of any of clauses 1-7, wherein the first white blood cellular component comprises the following positive control markers: MPO, CD79a, CD19, CD7, cytoplasmic CD3, cell surface CD3, CD20, Lambda light chain, Kappa light chain, CD4, CD8, CD5, TCRγδ, CD56, β2-Microglobulin.

9. The control composition of any of clauses 1-8, wherein the second cellular component comprises the following positive control markers: CD34, CD117, CD105, CD71, TdT.

10. The control composition of any of clauses 1-9, wherein the third cellular component comprises the following positive control markers: CD38, CD23, CD10, CD79b, CD200, CD43, CD56, CD45, CD28, CD27, CD81, CD138.

11. The control composition of any of clauses 1-10, wherein the first white blood cellular component comprises an amount of cells ranging from $2 \times 10^6$ to $3 \times 10^6$ cells.

12. The control composition of any of clauses 1-11, wherein the first white blood cellular component comprises white blood cells.

13. The control composition of any of clauses 1-12, wherein the first white blood cellular component is prepared from whole blood contacted with a lysing agent for lysing red blood cells.

14. The control composition of any of clauses 1-13, wherein the second cellular component comprises an amount of cells that ranges from 5-10% of total cells of the control composition.

15. The control composition of any of clauses 1-14, wherein the second cellular component comprises an amount of cells ranging from $0.1 \times 10^6$ to $0.3 \times 10^6$ cells.

16. The control composition of any of clauses 1-15, wherein the second cellular component comprises hematopoietic stem/progenitor cells.

17. The control composition of any of clauses 1-16, wherein the second cellular component comprises bone marrow cells.

18. The control composition of any of clauses 1-16, wherein the second cellular component comprises cord blood cells.

19. The control composition of any of clauses 1-18, wherein the third cellular component comprises an amount of cells that ranges from 5-10% of total cells in the control composition.

20. The control composition of any of clauses 1-19, wherein the third cellular component comprises an amount of cells ranging from $0.1 \times 10^6$ to $0.3 \times 10^6$ cells.

21. The control composition of any of clauses 1-20, wherein the third cellular component comprises neoplastic cells.

22. The control composition of clause 21, wherein the neoplastic cells comprise lymphoma cells, leukemia cells, or multiple myeloma cells.

23. The control composition of any of clauses 1-22, wherein the control composition comprises an amount of cells ranging from $2 \times 10^6$ to $3 \times 10^6$ cells.

24. The control composition of any of clauses 1-23, wherein the control composition is dried.

25. A method comprising:
performing a flow cytometric assay with the control composition according to any of clauses 1-23, the flow cytometric assay comprising:
contacting the control composition with one or more binding members specific to the one or more positive control markers to produce a labeled control composition; and
introducing the labeled control composition to a flow cytometer to generate flow cytometric data that indicates whether the one or more positive control markers were detected,
wherein flow cytometric data indicating detection of the one or more positive markers validates the functionality of the flow cytometric assay and the one or more binding members.

26. The method of clause 25, wherein the control composition is dried.

27. The method of clause 26, wherein the flow cytometric assay further comprises reconstituting the control composition with buffer.

28. The method of any of clauses 25-27, wherein the flow cytometric assay further comprises contacting the control composition with a permeabilizing agent.

29. The method of any of clauses 25-28, wherein the one or more binding members is conjugated to a detectible label.

30. The method of clause 29, wherein the detectible label comprises a fluorescent label.

31. The method of any of clauses 25-30, wherein the one or more binding members comprises an antibody.

32. A method of producing a control composition, the method comprising:
combining a first white blood cellular component comprising one or more positive control markers for white blood cells with a second cellular component comprising one or more positive control markers for hematopoietic stem/progenitor cells and a third cellular component comprising one or more positive control markers for neoplastic cells to produce a combined cellular composition; and
contacting the combined cellular composition with a fixing agent to produce a control composition.

33. The method of clause 32, wherein the method further comprises contacting an amount of whole blood with a lysing agent for lysing red blood cells to produce the first white blood cellular component.

34. The method of clause 33, wherein the amount of whole blood is contacted with the lysing agent for an amount of time ranging from 10 to 20 minutes.

35. The method of any of clauses 33-34, wherein the amount of whole blood is contacted with the lysing agent at a temperature ranging from 15-25 degrees Celsius.

36. The method of any of clauses 33-35, wherein the method further comprises washing the first white blood cellular component.

37. The method of clause 36, wherein the method further comprises centrifuging the first white blood cellular component.

38. The method of clause 37, wherein the method further comprises quantifying an amount of cells present in the first white blood cellular component.

39. The method of any of clauses 32-38, wherein the first white blood cellular component comprises an amount of cells ranging from $4 \times 10^7$ to $6 \times 10^7$ cells.

40. The method of any of clauses 32-39, wherein the first white blood cellular component comprises white blood cells.

41. The method of any of clauses 32-40, wherein the second cellular component comprises an amount of cells ranging from $4 \times 10^6$ to $5 \times 10^6$ cells.

42. The method of any of clauses 32-41, wherein the second cellular component comprises hematopoietic stem/progenitor cells.

43. The method of any of clauses 32-42, wherein the second cellular component comprises bone marrow cells.

44. The method of any of clauses 32-42, wherein the second cellular component comprises cord blood cells.

45. The method of any of clauses 32-44, wherein the third cellular component comprises an amount of cells ranging from $4 \times 10^6$ to $5 \times 10^6$ cells.

46. The method of any of clauses 32-45, wherein the third cellular component comprises neoplastic cells.

47. The method of clause 46, wherein the neoplastic cells comprise lymphoma cells, leukemia cells, or multiple myeloma cells.

48. The method of any of clauses 32-47, wherein the combined cellular composition is contacted with the fixing agent for an amount of time ranging from 30 minutes to 1.5 hours.

49. The method of any of clauses 32-48, wherein the combined cellular composition is contacted with the fixing agent at a temperature ranging from 15-25 degrees Celsius.

50. The method of any of clauses 32-49, wherein the method further comprises washing the control composition.

51. The method of clause 50, wherein the method further comprises centrifuging the control composition.

52. The method of clause 51, wherein the method further comprises reconstituting the control composition with buffer.

53. The method of clause 52, wherein the method further comprises quantifying an amount of cells present in the control composition.

54. The method of any of clauses 32-53, wherein the control composition comprises an amount of cells ranging from $4 \times 10^7$ to $6 \times 10^7$ cells.

55. The method of any of clauses 53-54, wherein the method further comprises centrifuging the control composition.

56. The method of clause 55, wherein the method further comprises reconstituting the control composition with buffer.

57. The method of clause 56, wherein the method further comprises drying the control composition.

58. The method of any of clauses 32-57, wherein the one or more positive control markers comprise cell surface markers.

59. The method of any of clauses 32-58, wherein the one or more positive control markers comprise intracellular markers.

60. The method of any of clauses 32-59, wherein the control composition comprises 50% or more of the positive control markers selected from the group consisting of: MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

61. The method of any of clauses 32-60, wherein the control composition comprises 60% or more of the positive control markers selected from the group consisting of: MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

62. The method of any of clauses 32-61, wherein the control composition comprises at 80% or more positive of the control markers selected from the group consisting of: MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

63. The method of any of clauses 32-62, wherein the control composition comprises MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

64. The method of any of clauses 32-63, wherein the first white blood cellular component comprises the following positive control markers: MPO, CD79a, CD19, CD7, cytoplasmic CD3, cell surface CD3, CD45, CD20, Lambda light chain, Kappa light chain, CD38, CD4, CD8, CD5, TCRγδ, CD56, β2-Microglobulin, CD138.

65. The method of any of clauses 32-64, wherein the second cellular component comprises the following positive control markers: CD34, CD117, CD105, CD71, TdT.

66. The method of any of clauses 32-65, wherein the third cellular component comprises the following positive control markers: CD38, CD23, CD10, CD79b, CD200, CD43, CD56, CD45, CD28, CD27, CD81, CD138.

67. The method of any of clauses 32-66, wherein the amount of cells in the second cellular component ranges from 5-10% of total cells of the control composition.

68. The method of any of clauses 32-67, wherein the amount of cells in the third cellular component ranges from 5-10% of total cells in the control composition.

69. A kit comprising:
a container comprising a control composition according to any of clauses 1-24.

70. The kit of clause 69, wherein the kit further comprises one or more containers comprising one or more binding members specific to the one or more positive control markers.

71. The kit of clause 70, wherein the one or more binding members is conjugated to a detectible label.

72. The kit of clause 71, wherein the detectible label comprises a fluorescent label.

73. The kit of any of clauses 70-72, wherein the one or more binding members comprises an antibody.

74. The kit of any of clauses 69-73, wherein the one or more containers comprise binding members specific to MPO, CD79a, CD34, CD19, CD7, cytoplasmic CD3, cell surface CD3, and CD45.

75. The kit of any of clauses 69-73, wherein the one or more containers comprise binding members specific to CD45, CD19, CD20, Lambda light chain, Kappa light chain, CD38, CD3, CD4, CD8, CD5, TCRγδ, and CD56.

76. The kit of any of clauses 69-73, wherein the one or more containers comprise binding members specific to CD23, CD10, CD79b, CD19, CD200, CD43, CD20, and CD45.

77. The kit of any of clauses 69-73, wherein the one or more containers comprise binding members specific to CD38, CD56, β2-Microglobulin, CD19, Anti-Kappa, Anti-Lambda, CD45, and CD138.

78. The kit of any of clauses 69-73, wherein the one or more containers comprise binding members specific to CD38, CD28, CD27, CD19, CD117, CD81, CD45, and CD138.

79. The kit of any of clauses 69-73, wherein the one or more containers comprise binding members specific to CD34, CD117, CD71, CD105, TdT, and CD138.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A control composition comprising:
    a first white blood cellular component comprising white blood cells comprising one or more positive control markers for white blood cells;
    a second hematopoietic stem/progenitor cellular component comprising hematopoietic stem/progenitor cells comprising one or more positive control markers for hematopoietic stem/progenitor cells; and
    a third neoplastic cellular component comprising neoplastic cells comprising one or more positive control markers for neoplastic cells,
    wherein the first white blood cellular component, the second cellular component, and third cellular component are fixed.

2. The control composition of claim 1, wherein at least one of the positive control markers in the control composition is a cell surface marker.

3. The control composition of claim 1, wherein at least one of the positive control markers in the control composition is an intracellular marker.

4. The control composition of claim 1, wherein the control composition comprises 50% or more of the positive control markers selected from the group consisting of: MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

5. The control composition of claim 1, wherein the control composition comprises 60% or more of the positive control markers selected from the group consisting of: MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

6. The control composition of claim 1, wherein the control composition comprises 80% or more of the positive control markers selected from the group consisting of: MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

7. The control composition of claim 1, wherein the control composition comprises the following positive control markers: MPO, CD79a, CD34, CD19, CD7, cytoplasmic CD3, cell surface CD3, CD45, CD20, Lambda light chain, Kappa light chain, CD38, CD4, CD8, CD5, TCRγδ, CD56, CD23, CD10, CD79b, CD200, CD43, CD20, β2-Microglobulin, CD138, CD28, CD27, CD117, CD81, CD71, CD105, TdT.

8. The control composition of claim 1, wherein the first white blood cellular component comprises the following positive control markers: MPO, CD79a, CD19, CD7, cytoplasmic CD3, cell surface CD3, CD20, Lambda light chain, Kappa light chain, CD4, CD8, CD5, TCRγδ, CD56, β2-Microglobulin.

9. The control composition of claim 1, wherein the second hematopoietic stem/progenitor cellular component comprises the following positive control markers: CD34, CD117, CD105, CD71, TdT.

10. The control composition of claim 1, wherein the third neoplastic cellular component comprises the following positive control markers: CD38, CD23, CD10, CD79b, CD200, CD43, CD56, CD45, CD28, CD27, CD81, CD138.

11. The control composition of claim 1, wherein the second cellular component comprises bone marrow cells.

12. The control composition of claim 1, wherein the control composition is dried.

13. The control composition of claim 1, wherein the second cellular component comprises cord blood cells.

14. A method comprising:
    performing a flow cytometric assay with the control composition according to claim 1, the flow cytometric assay comprising:
        contacting the control composition with one or more binding members specific to the one or more positive control markers to produce a labeled control composition; and
        introducing the labeled control composition to a flow cytometer to generate flow cytometric data that indicates whether the one or more positive control markers were detected,
    wherein flow cytometric data indicating detection of the one or more positive markers validates the functionality of the flow cytometric assay and the one or more binding members.

15. The method of claim 14, wherein the control composition is dried.

16. The method of claim 15, wherein the flow cytometric assay further comprises reconstituting the control composition with buffer.

17. The method of claim 14, wherein the flow cytometric assay further comprises contacting the control composition with a permeabilizing agent.

18. The method of claim 14, wherein the one or more binding members is conjugated to a detectible label.

* * * * *